(12) United States Patent
Park et al.

(10) Patent No.: US 10,126,232 B2
(45) Date of Patent: *Nov. 13, 2018

(54) SAMPLE TEST METHOD, MICROFLUIDIC DEVICE, AND TEST DEVICE

(71) Applicant: SAMSUNG ELECTRONICS CO., LTD., Suwon-si (KR)

(72) Inventors: Sung Ha Park, Suwon-si (KR); Sang Bum Park, Hwaseong-si (KR); Beom Seok Lee, Osan-si (KR); Kui Hyun Kim, Hwaseong-si (KR); Joo Hee Park, Yongin-si (KR); Kyung Mi Song, Suwon-si (KR); Euy Hyun Cho, Suwon-si (KR); Ha Na Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/891,632

(22) Filed: Feb. 8, 2018

(65) Prior Publication Data

US 2018/0180536 A1 Jun. 28, 2018

Related U.S. Application Data

(63) Continuation of application No. 14/824,180, filed on Aug. 12, 2015, now Pat. No. 9,927,351.

(30) Foreign Application Priority Data

Aug. 12, 2014 (KR) .................. 10-2014-0104285
Dec. 30, 2014 (KR) .................. 10-2014-0194091

(51) Int. Cl.
*G01N 21/31* (2006.01)
*G01N 21/05* (2006.01)
(Continued)

(52) U.S. Cl.
CPC ............. *G01N 21/31* (2013.01); *G01N 21/05* (2013.01); *G01N 21/274* (2013.01);
(Continued)

(58) Field of Classification Search
CPC ....... B01L 2300/024; B01L 2300/0806; B01L 2300/0864; B01L 2300/0887;
(Continued)

(56) References Cited

U.S. PATENT DOCUMENTS 4,167,449 A 9/1979 Gargiulo et al.
4,177,109 A 12/1979 Tohyama et al.
(Continued)

FOREIGN PATENT DOCUMENTS

WO 2005/027746 A1 3/2005

OTHER PUBLICATIONS

Communication dated Jan. 23, 2018, issued by the European Patent Office in counterpart European application No. 15832169.5.
(Continued)

*Primary Examiner* — Maureen Wallenhorst
(74) *Attorney, Agent, or Firm* — Sughrue Mion, PLLC

(57) ABSTRACT

A sample test method, microfluidic device, and test device efficiently and accurately compensates for interference of an interfering substance present in a sample using optical measurement without addition of a separate reagent for detecting the interfering substance. The sample test method includes: measuring an optical characteristic value of a target substance present in a sample; measuring an optical characteristic value of an interfering substance present in the sample; and determining a concentration of the target substance for which interference of the interfering substance is compensated for based on the optical characteristic value of the interfering substance.

13 Claims, 35 Drawing Sheets

(51) Int. Cl.
*G01N 21/27* (2006.01)
*G01N 21/01* (2006.01)
*G01N 33/49* (2006.01)
*G01N 33/08* (2006.01)
*G01N 35/08* (2006.01)
*B01L 3/00* (2006.01)

(52) U.S. Cl.
CPC ......... *G01N 21/314* (2013.01); *G01N 33/492* (2013.01); *B01L 3/5023* (2013.01); *B01L 3/50273* (2013.01); *B01L 3/502715* (2013.01); *B01L 2200/025* (2013.01); *B01L 2200/04* (2013.01); *B01L 2200/148* (2013.01); *B01L 2200/16* (2013.01); *B01L 2300/024* (2013.01); *B01L 2300/0806* (2013.01); *B01L 2300/0864* (2013.01); *B01L 2300/0887* (2013.01); *B01L 2300/161* (2013.01); *B01L 2400/0409* (2013.01); *G01N 2021/3129* (2013.01); *G01N 2333/9108* (2013.01); *Y10T 436/146666* (2015.01)

(58) Field of Classification Search
CPC ............. B01L 2300/161; B01L 3/5023; B01L 3/502715; B01L 3/50273; B01L 3/5027; B01L 2400/0409; B01L 2200/025; B01L 2200/04; B01L 2200/148; B01L 2200/16; G01N 2021/3129; G01N 21/05; G01N 21/274; G01N 21/31; G01N 21/314; G01N 2333/91; G01N 2333/9108; G01N 33/49; G01N 33/492; G01N 33/52; Y10T 436/146666
USPC ............. 436/63, 97, 164; 422/82.05, 82.09; 435/15, 29, 288.7; 356/39, 409
See application file for complete search history.

(56) References Cited

U.S. PATENT DOCUMENTS

| | | | |
|---|---|---|---|
| 4,263,512 | A | 4/1981 | Sagusa et al. |
| 6,115,673 | A | 9/2000 | Malin et al. |
| 6,207,459 | B1 | 3/2001 | Weisheit et al. |
| 6,268,167 | B1 | 7/2001 | Wild et al. |
| 7,198,955 | B1 | 4/2007 | Samsoondar et al. |
| 9,927,351 | B2 * | 3/2018 | Park ................ G01N 21/31 |
| 2014/0193921 | A1 | 7/2014 | Lee et al. |
| 2016/0187363 | A1 | 6/2016 | Kim |

OTHER PUBLICATIONS

Search Report dated Nov. 27, 2015, issued by the International Searching Authority in counterpart International Patent Application No. PCT/KR2015/008397 (PCT/ISA/210).

* cited by examiner

FIG. 25

| SAMPLE | Cl mg/dL | Cl mg/mol BEFORE ELIMINATION OF T-Bil INTERFERENCE | T-bil mg/dL at TEST DEVICE(100) | Cl mg/mol at TEST DEVICE(100) AFTER ELIMINATION OF T-Bil INTERFERENCE | BIAS BEFORE IMPROVEMENT | BIAS AFTER IMPROVEMENT |
|---|---|---|---|---|---|---|
| A | 89 | 116 | 10.4 | 95 | 30.30% | 7.00% |
| B | 92 | 104 | 4.1 | 96 | 13.10% | 4.20% |
| C | 98 | 110 | 4.1 | 102 | 12.20% | 3.90% |
| D | 106 | 112 | 2.2 | 107 | 5.60% | 1.40% |
| E | 85 | 91 | 3.4 | 84 | 7.20% | 0.80% |
| F | 85 | 91 | 1.6 | 88 | 7.20% | 3.50% |
| G | 89 | 98 | 1.6 | 95 | 10.30% | 6.70% |

SAMPLE TEST METHOD, MICROFLUIDIC DEVICE, AND TEST DEVICE

CROSS-REFERENCE TO RELATED APPLICATION

This is a continuation of U.S. patent application Ser. No. 14/824,180 filed Aug. 12, 2015, now U.S. Pat. No. 9,927,351, which claims priority under from Korean Patent Application No. 10-2014-0104285 filed on Aug. 12, 2014 and Korean Patent Application No. 10-2014-0194091 filed on Dec. 30, 2014. The entire disclosures of the prior applications are considered part of the disclosure of the accompanying continuation application, and are hereby incorporated by reference.

TECHNICAL FIELD

Apparatuses and methods consistent with exemplary embodiments relate to a sample test method, microfluidic device, and test device capable of in vitro diagnostics.

BACKGROUND

In Vitro Diagnostics (IVD) may be performed through immunity tests, clinical chemistry tests, etc., on patient samples, and plays an important role in diagnosis and treatment on the patient's disease and determination of patient convalescence.

IVD may be performed by measuring the concentration of a certain target substance present in the patient sample. Reactions between a reagent and the sample may be used for IVD. However, because other various substances in addition to the target substance are also present in the sample and act as interfering substances, reactions for detecting the target substance may be hampered or overreactions may occur.

Accordingly, a need exists for development of a method for compensating for effects of the interfering substances present in the sample.

SUMMARY

Exemplary embodiments provide a sample test method, microfluidic device, and test device for efficiently and accurately compensating for interference of an interfering substance present in a sample with optical measurement without addition of a separate reagent for detecting the interfering substance.

In accordance with an aspect of an exemplary embodiment, a sample test method is provided. The sample test method includes measuring an optical characteristic value of a target substance present in a sample; measuring an optical characteristic value of an interfering substance present in the sample; and determining a concentration of the target substance for which interference of the interfering substance is compensated for based on the optical characteristic value of the interfering substance.

The determining the concentration of the target substance for which interference of the interfering substance is compensated for may include compensating the optical characteristic value of the target substance using the optical characteristic value of the interfering substance, and determining the concentration of the target substance based on the compensated optical characteristic value.

The compensating the optical characteristic value of the target substance may include applying a fluctuation coefficient to the optical characteristic value of the interfering substance to obtain an application result, and then subtracting or adding the application result from or to the optical characteristic value of the target substance.

The measuring the optical characteristic value of the target substance may include measuring optical characteristic values of the target substance at a main wavelength and a sub-wavelength; and subtracting the optical characteristic value at the sub-wavelength from the optical characteristic value at the main wavelength.

The main wavelength and the sub-wavelength may be each chosen from a range of 300 nm to 900 nm.

The sample may include blood, and the target substance may include gamma-glutamyl transferase (GGT).

The measuring the optical characteristic value of the interfering substance may include measuring optical characteristic values of the sample at a plurality of wavelengths, and determining a final optical characteristic value from the measured optical characteristic values, wherein the final optical characteristic value may be an optical characteristic value for the interfering substance.

The plurality of wavelengths may be chosen in 400 nm band, 500 nm band, and 600 nm band, respectively.

The determining the final optical characteristic value may include subtracting respective optical characteristic values measured at a wavelength in the 500 nm band and at a wavelength in the 600 nm band from an optical characteristic value measured at a wavelength in the 400 nm band.

The measuring an optical characteristic value of the interfering substance may include measuring an optical characteristic value of the sample at a wavelength in 800 nm band.

The determining the final optical characteristic value may include subtracting the optical characteristic value measured at a wavelength in the 800 nm band from an optical characteristic value measured at a wavelength in the 400 nm band, subtracting the optical characteristic value measured at a wavelength in the 800 nm band from an optical characteristic value measured at a wavelength in the 500 nm band, and subtracting the optical characteristic value measured at a wavelength in the 800 nm band from an optical characteristic value measured at a wavelength in the 600 nm band.

The determining the final optical characteristic value may include subtracting a value resulting from the subtraction of the optical characteristic value measured at a wavelength in the 800 nm band from the optical characteristic value measured at a wavelength in the 500 nm band, and a value resulting from the subtraction of the optical characteristic value measured at a wavelength in the 800 nm band from the optical characteristic value measured at a wavelength in the 600 nm band from a value resulting from the subtraction of the optical characteristic value measured at a wavelength in the 800 nm band from the optical characteristic value measured at a wavelength in the 400 nm band.

The interfering substance may include bilirubin.

The determining a concentration of the target substance for which interference of the interfering substance is compensated for may include compensating the optical characteristic value of the target substance using the optical characteristic value of the interfering substance, and determining the concentration of the target substance based on the compensated optical characteristic value.

The determining the concentration of the target substance for which interference of the interfering substance is compensated for may include determining the concentration of the target substance based on the optical characteristic value of the target substance, determining the concentration of the interfering substance based on the optical characteristic value of the interfering substance, and compensating the concentration of the target substance using the concentration of the interfering substance.

The measuring the optical characteristic value of the interfering substance may be done without the presence of a reagent for reacting with the interfering substance.

The optical characteristic values may be representative of concentration of at least one of the target substance and the interfering substance, and the sample test method is performed using one or more processors.

In accordance with an aspect of another exemplary embodiments, a test device is provided. The test device may include a measurer configured to measure an optical characteristic value of a target substance present in a sample and an optical characteristic value of an interfering substance present in the sample; and a data processor configured to determine a concentration of the target substance for which interference of the interfering substance is compensated for based on the optical characteristic value of the interfering sub stance.

The data processor may be configured to compensate the optical characteristic value of the target substance using the optical characteristic value of the interfering substance, and determine the concentration of the target substance based on the compensated optical characteristic value.

The data processor may be configured to apply a fluctuation coefficient to the optical characteristic value of the interfering substance to obtain an application result, and then subtract or add the application result from or to the optical characteristic value of the target substance.

The measurer may be configured to measure optical characteristic values of the target substance at a main wavelength and a sub-wavelength; and the data processor may subtract the optical characteristic value measured at the sub-wavelength from the optical characteristic value measured at the main wavelength.

The main wavelength and the sub-wavelength may be each chosen from a range of 300 nm to 900 nm.

The sample may include blood, and the target substance may include gamma-glutamyl transferase (GGT).

The measurer may be configured to measure optical characteristic values of the sample at a plurality of wavelengths, and the data processor may determine a final optical characteristic value from the measured optical characteristic values of the sample, wherein the final optical characteristic value may be an optical characteristic value for the interfering sub stance.

The plurality of wavelengths may be chosen in 400 nm band, 500 nm band, and 600 nm band, respectively.

The data processor may subtract respective optical characteristic values measured at a wavelength in the 500 nm band and at a wavelength in the 600 nm band from an optical characteristic value measured at a wavelength in the 400 nm band.

The measurer may be configured to measure an optical characteristic value of the sample at a wavelength in 800 nm band.

The data processor may be configured to determine the final optical characteristic value by subtracting the optical characteristic value measured at a wavelength in the 800 nm band from an optical characteristic value measured at a wavelength in the 400 nm band, subtracting the optical characteristic value measured at a wavelength in the 800 nm band from an optical characteristic value measured at a wavelength in the 500 nm band, and subtracting the optical characteristic value measured at a wavelength in the 800 nm band from an optical characteristic value measured at a wavelength in the 600 nm band.

The data processor may determine the final optical characteristic value by subtracting a value resulting from the subtraction of the optical characteristic value measured at a wavelength in the 800 nm band from the optical characteristic value measured at a wavelength in the 500 nm band, and a value resulting from the subtraction of the optical characteristic value measured at a wavelength in the 800 nm band from the optical characteristic value measured at a wavelength in the 600 nm band from a value resulting from the subtraction of the optical characteristic value measured at a wavelength in the 800 nm band from the optical characteristic value measured at a wavelength in the 400 nm band.

The interfering substance may include bilirubin.

The data processor may be configured to compensate the optical characteristic value of the target substance using the optical characteristic value of the interfering substance, and determine the concentration of the target substance based on the compensated optical characteristic value.

The data processor may be configured to determine the concentration of the target substance based on the optical characteristic value of the target substance, determine the concentration of the interfering substance based on the optical characteristic value of the interfering substance, and compensate the concentration of the target substance using the concentration of the interfering substance.

In accordance with an aspect of another exemplary embodiments, a microfluidic device is provided. The microfluidic device includes a platform formed with a sample inlet hole into which a sample is injected; a plurality of chambers each of the chambers having a different depth; and a channel connecting the sample inlet hole and the plurality of chambers.

In accordance with an aspect of another exemplary embodiments, a test device is provided. The test device includes a measurer configured to measure optical characteristic values of a sample in a plurality of wavelength bands; and a data processor for configured to determine a final optical characteristic value from the measured optical characteristic values, and determine a concentration of bilirubin present in the sample based on the determined final optical characteristic value.

The plurality of wavelength bands may include 400 nm, 500 nm, and 600 nm bands.

The data processor may be configured to subtract respective optical characteristic values measured at a wavelength in the 500 nm band and at a wavelength in the 600 nm band from an optical characteristic value measured at a wavelength in the 400 nm band.

The measurer may be configured to measure respective optical characteristic values of the sample a particular wavelength, for a plurality of light paths, each light path having a different length.

The controller may be configured to select a light path from the light paths of different lengths based on the measured optical characteristic values.

The controller may select a light path that satisfies linearity as related to the measured optical characteristic values of the plurality of light paths and has the longest light path length from among the measured optical characteristic values.

The test device may receive a test platform, the test platform having plural chambers, each chamber having a different depth, to provide the plurality of light paths.

BRIEF DESCRIPTION OF THE DRAWINGS

The above and other aspects will become more apparent by describing in detail exemplary embodiments with reference to the attached drawings in which:

FIG. 25 is a table representing respective concentrations of chloride and bilirubin measured by a standard device and a test device in accordance with an exemplary embodiment;

Throughout the drawings, like reference numerals will be understood to refer to like parts, components, and structures.

DETAILED DESCRIPTION

Figure 1:
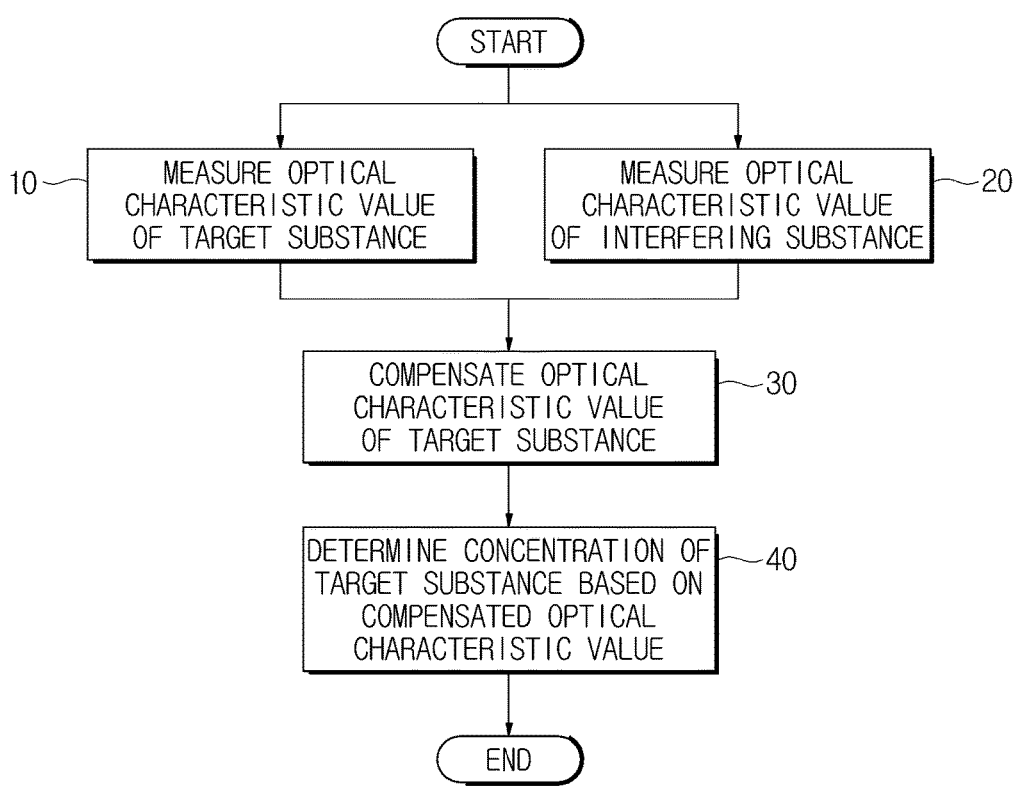
FIG. 1 is a flowchart illustrating a sample test method, according to an exemplary embodiment.

Exemplary embodiments will now be described with reference to accompanying drawings.

A sample test method, microfluidic device, and test device in accordance with exemplary embodiments may be applied for IVD that uses samples taken from a subject, and immunity tests, clinical chemistry tests, etc., may be performed for IVD.

For example, a blood sample may be taken for IVD, and there are many different substances contained in the blood sample. For example, bilirubin contained in the blood is one of the constituents of bile, which is mainly produced by hemoglobin. The concentration of bilirubin increases when the patient has hepatitis, cirrhosis, liver cancer, biliary obstruction, etc., and the increase of bilirubin concentration in blood causes jaundice. Accordingly, bilirubin levels in blood may be an important index for a liver function test.

IVD measurement items may also include measurement of substances other than bilirubin, such as creatinine measurement, electrolyte measurement, etc., for assessing a kidney function. Bilirubin in blood even influences measurements of other substances, which is called bilirubin interference.

In a case that a measurement item is bilirubin or that bilirubin interference is to be eliminated from measurements of other measurement items, it is necessary to quantitatively and accurately measure the concentration of total bilirubin present in the sample, and to promptly perform measurement of the concentration of bilirubin or even elimination of its interference to fit the IVD characteristics in need of faster test results.

In another example, gamma glutamyl transferase (GGT) is an enzyme widely distributed in many tissues, such as the kidneys, pancreas, prostate, liver, etc. GGT is activated to increase the in blood-GGT level in the body of a patient who suffers from obstructive jaundice, liver cancer, or alcoholic liver disease. Therefore, GGT may be included as a measurement item in the IVD measurement list, and the GGT level is measured to be used in diagnosis of obstructive jaundice, liver cancer, etc. However, accurate measurement of GGT level may be hampered by interference of other interfering substances present in the sample. For example, if the concentration of hemoglobin present in the sample is high or the sample is hemolytic, accurate measurement is disrupted significantly by the interfering substances.

In an exemplary embodiment, a sample test method and test device may eliminate interference of the interfering substances other than a target substance present in the sample, with optical measurement without addition of a separate reagent in measuring the concentration of the target substance. The target substance refers to a substance subject to measurement among substances present in the sample, e.g., a substance that is a measurement item, and an interfering substance refers to a substance that influences the measurement of the concentration of the target substance among substances present in the sample other than the target substance.

FIG. 1 is a flowchart illustrating a sample test method, according to an exemplary embodiment.

Referring to FIG. 1, an optical characteristic value of a target substance is measured in operation 10, and an optical characteristic value of an interfering substance is measured in operation 20. The optical characteristic values may be measured while the sample is contained in a chamber or chambers. The optical characteristic values measured can include optical density indicating a degree to which a substance absorbs light, reflectivity indicating a degree to which a substance reflects light, transmittance indicating a degree to which light passes through a substance, or other various optical values.

The optical characteristic values of the target and interfering substances may be measured simultaneously or sequentially, depending on the structure of the test device as will be described below. As for the sequential measurement, there is no limitation on whether the optical characteristic value of the target substance is measured first or that of the interfering substance is measured first.

The optical characteristic value of the target substance may be an optical characteristic value that appears due to a reaction between the sample and a particular reagent, or may be an optical characteristic value of the sample itself. In the former case, the particular reagent may include a substance that singularly or selectively reacts with the target substance, or a substance with which the reaction is catalyzed by the target substance, or a substance with which reaction is catalyzed by a substance activated by the target substance. In the latter case, optical characteristics of the target substance itself contained in the sample is measured without use of a reagent.

The optical characteristic value of the interfering substance may be one of the sample itself. In other words, without use of a separate reagent for detecting the interfering substance, the optical characteristic value of the interfering substance may be measured by controlling the wavelength of light used for measurement of the optical characteristic value.

The optical characteristic value of the target substance is compensated using the optical characteristic value of the interfering substance, in operation 30. Specifically, the product of the optical characteristic value of the interfering substance multiplied by a predetermined coefficient may be subtracted from or added to the optical characteristic value of the target substance. The predetermined coefficient as used herein is assumed to be a fluctuation coefficient.

The concentration of the target substance is then estimated or calculated. Specifically, the concentration of the target substance is determined based on the compensated optical characteristic value of the target substance, in operation 40. For example, the concentration of the target substance may be determined by applying the optical characteristic value onto a pre-stored calibration curve. The calibration curve may represent relations between optical characteristic values and concentrations of a target substance. A method for determining a concentration based on the optical characteristic value is divided into an end point-based method and a kinetic-based method. In the exemplary embodiment, it is assumed that a proper one of the end point-based method and the kinetic-based method is used.

While compensation is performed based on the optical characteristic value in the example of FIG. 1, concentration-based compensation is also possible. Specifically, compensation may also be made by determining the concentration of a target substance from the optical characteristic value of the target substance, determining the concentration of an interfering substance from the optical characteristic value of the interfering substance, and then adding or subtracting a value resulting from application of a fluctuation coefficient to the concentration of the interfering substance to or from the concentration of the target substance.

A test device in accordance with an exemplary embodiment will now be described. The test device may be used to perform tests according to the sample test method as described in connection with FIG. 1, so the description of FIG. 1 may be equally applied to this test device.

Figure 2:
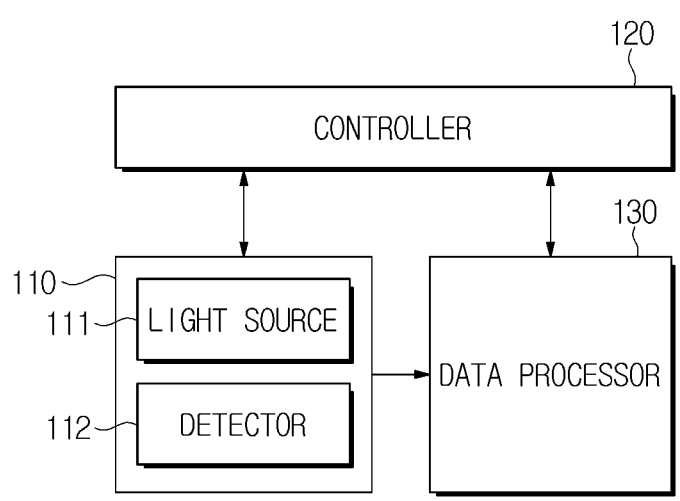
FIG. 2 is a control block diagram of a test device, according to an exemplary embodiment.

FIG. 2 is a control block diagram of a test device, according to an exemplary embodiment.

Referring to FIG. 2, a test device 100 in accordance with an exemplary embodiment may include a measurer 110 for measuring an optical characteristic value at a particular wavelength, a data processor 130 for determining the concentration of a target substance contained in a sample based on measured optical characteristic values, and a controller 120 for controlling overall operation of the test device 100. The controller can be implemented in hardware such as a computing unit, integrated circuit, combination of hard and software, etc.

The measurer 110 may include a light source 111 for producing and irradiating light, and a detector 112 for detecting light transmitted through or reflected from the sample.

For example, the light source 111 may include a Light Emitting Diode (LED), or may be implemented with any other light source of a different type, such as semiconductor laser, He—Ne laser, halogen lamp, etc. The measurer 110 may further include an additional device, such as a filter for irradiating light of a particular wavelength.

Light of a desired wavelength in the band of 300 nm to 800 nm may be irradiated from the light source 111, and a proper wavelength may be selected based on types of target and interfering substances and a scheme applied for concentration measurement.

The detector 112 may detect light transmitted through the sample, and convert the detected light to an electric signal based on the intensity of the detected light. For this, the detector 112 may include a light receiving element like a photo diode. It may also convert the electric signal to an optical characteristic value, such as optical density, transmittance, reflectivity, etc., and output the result to the data processor 130. For this, the detector 112 may further include an operation device like a microprocessor. Alternatively, the detector 112 may output the electric signal, and the data processor 130 may then convert the electric signal to an optical characteristic value, such as optical density and subsequently perform an operation for measurement of the concentration of a measurement item.

The controller 120 may control general operations of the test device 100. For example, it may control the wavelength of light irradiated from the measurer 110, or control the position of the measurer 110 to a position corresponding to a chamber that contains the sample, or control the rotation of the chamber if it is required to test the sample.

Furthermore, if the data processor 130 measures the concentration of a measurement item or perform diagnosis on a particular disease based on a value output from the detector 112, the controller 120 may control the results to be displayed, if any.

The data processor 130 and controller 120 may include a memory to store a program associated with aforementioned or following operations, and a processor to run the program stored in the memory. It is possible for the data processor 130 and controller 120 to each have at least one memory and processor, or to share the memory and processor.

Operation of the test device 100 will be described in detail with reference to views of appearance of the microfluidic device and test device 100 that contain a sample.

Figure 3:
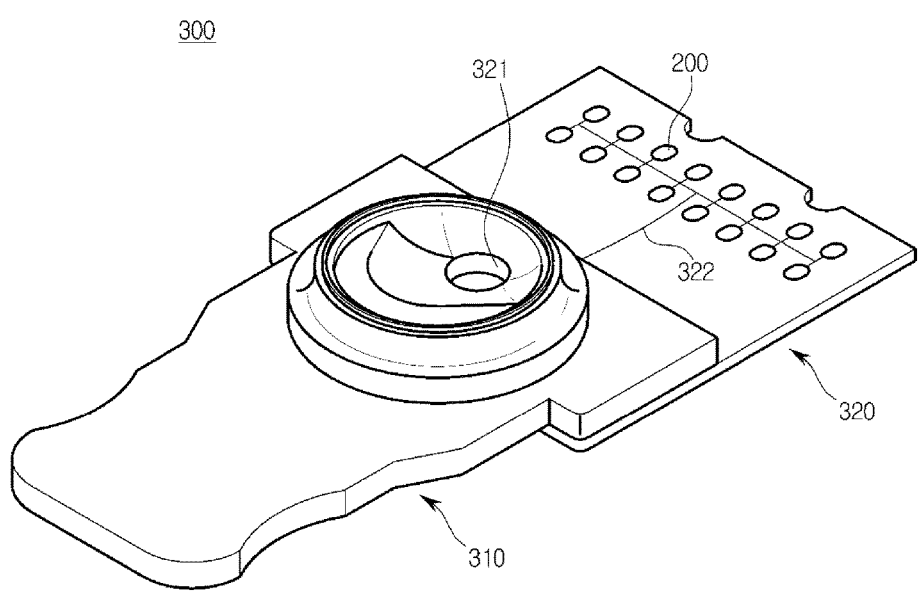
FIG. 3 is a view of appearance of an exemplary microfluidic device, according to an exemplary embodiment.
Figure 4:
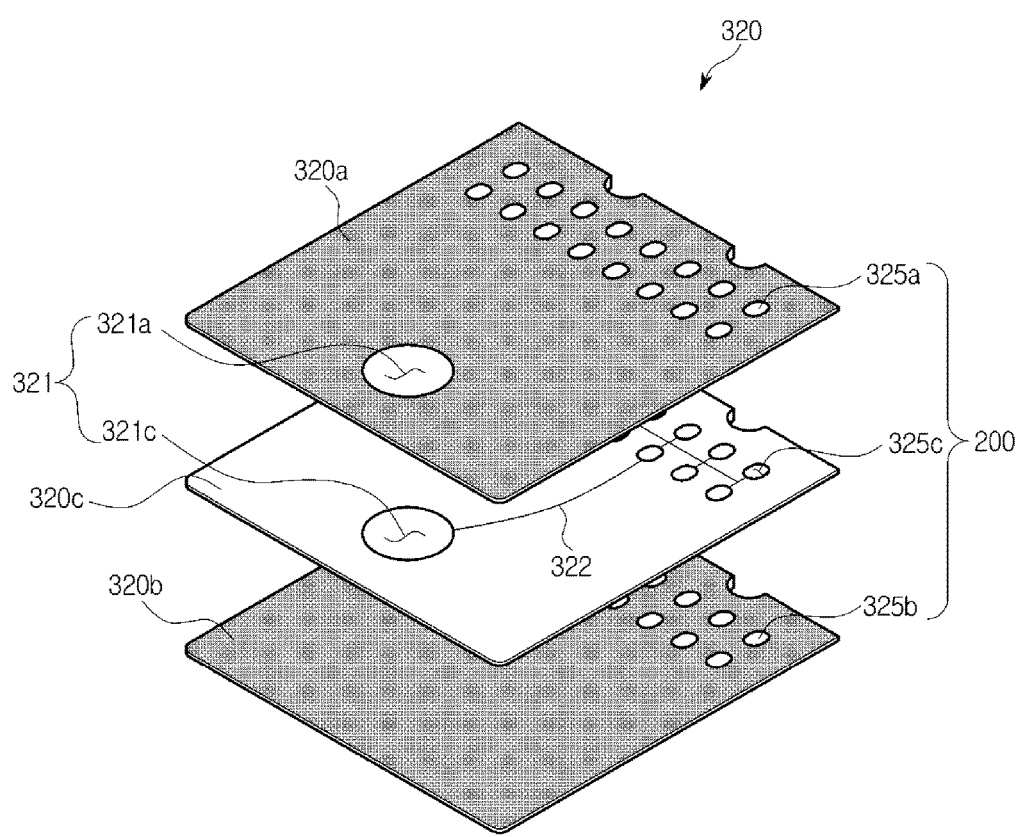
FIG. 4 is an exploded view of a structure of a platform of the microfluidic device of FIG. 3.

FIG. 3 is a view of appearance of an exemplary microfluidic device, according to an exemplary embodiment, and FIG. 4 is an exploded view of a structure of a platform of the microfluidic device of FIG. 3. Referring to FIG. 3, a microfluidic device 300 in accordance with an exemplary embodiment may be implemented in a cartridge type, which includes a housing 310 and a platform 320 on which optical measurement is performed on a sample.

The housing 310 allows the user to hold the microfluidic device 300 while supporting the platform 320. The housing 310 is easy to be molded, and may be formed of an chemically and biologically inactive material.

For example, various materials including plastic materials, such as acryl, e.g., polymethylmethacrylate (PMMA), polysiloxane, e.g., polydimethylsiloxane (PDMS), polycarbonate (PC), linear low density polyethylene (LLDPE), low density polyethylene (LDPE), medium density polyethylene (MDPE), high density polyethylene (HDPE), polyvinyl alcohol, very low density polyethylene (VLDPE), polypropylene (PP), acrylonitrile butadiene styrene (ABS), cycloolefin copolymer (COC), etc., glass, mica, silica, semiconductor wafer, etc., may be used as the material for the housing 310. However, the material for the housing 310 is not limited thereto.

The platform 320 may be combined with the housing 310 in such a way as to be connected to the bottom of the housing 310, or to be inserted into a groove formed in the housing 310.

A sample inlet hole 321 is formed on the platform 320 for a sample to be injected thereto. A sample to be provided for the microfluidic device 300 may be a biosample, e.g., body fluids including blood, tissue fluids, lymph fluids, urine, saliva, marrow, or the like, and a target substance subject to concentration measurement may be electrolyte ions or enzymes present in the sample.

The user may use a tool, e.g., a pipet or a syringe to drop a sample into the sample inlet hole 321 for tests.

The sample injected into the sample inlet hole 321 flows into the inside of the platform 320, and in this regard, although not shown, a filter is placed behind the sample inlet hole 321 to filter the injected sample. The filter may be a porous polymeric membrane formed of, e.g., PC, polyethersulfone (PES), polyethylene (PE), polysulfone (PS), polyaryl sulfone (PASF), etc. For example, if a blood sample is injected, blood corpuscle is filtered out but blood plasma or blood serum flows into the inside of the platform 320 as the blood is passed through the filter.

Referring to FIG. 4, the platform 320 may be formed in a structure in which three plates 320a, 320b, 320c are joined together. The three plates may include a top plate 320a, a bottom plate 320b, and a middle plate 320c, and the top and bottom plates 320a and 320b may be printed with light-shielding ink to protect the sample being moved to the chamber 200 from outside light.

The top and bottom plates 320a and 320b may be made in the form of film, and the film used to form the top and bottom plates 320a and 320b may be one selected from among polyethylene films, such as VLDPE, LLDPE, LDPE, MDPE, HDPE, etc., polyvinyl chloride (PVC) films, polyvinyl alcohol (PVA) films, polystyrene films, and polyethylene terephthalate (PET) films.

The middle plate 320c of the platform 320 may be formed of a porous sheet, such as cellulose to serve as a vent in itself, and the porous sheet may be made of a hydrophobic material or hydrophobic process is applied on the porous sheet in order not to influence the movement of the sample.

In the platform 320, the sample inlet hole 321, a channel through which the injected sample is moved, and a plurality of chambers 200. In a case that the platform 320 is formed in a triple layered structure, a top hole 321a that constitutes the sample inlet hole 321 is formed on the top plate 320a, and portions 325a corresponding to the chambers 200 may be processed to be transparent.

The bottom plate 320b may also have portions 325b corresponding to the chambers 200 processed transparently. Processing the portions 325a, 325b to be transparent is to measure optical characteristics of the sample contained in the chambers 200 or optical characteristics due to reactions that occur in the chambers 200.

Even in the middle plate 320c, a middle plate hole 321c that constitutes the sample inlet hole 321 is formed, and when the top, middle, and bottom plates 320a, 320c, and 320b are joined together, the top and middle plate holes 321a and 321c overlap to form the sample inlet hole 321 of the platform 320.

In the area of the middle plate 320c, chambers 200 are formed in the opposite side to the middle plate hole 321c, and the chambers 200 may be formed by trimming the portions corresponding to the chambers 200 into a certain shape like circle, square, etc., and then joining the top, middle, and bottom plates 320a, 320c, and 320b together.

Furthermore, the channel 322 is formed on the middle plate 320c to be 1 μm to 500 μm wide, in order for the sample injected into the sample inlet hole 321 to be moved to the chambers 200 by capillary attraction. However, the width of the channel 322 is merely an example to be used in the microfluidic device 300, and exemplary embodiments are not limited thereto.

Some of the plurality of chambers 200 may contain respective reagents for the use of the chamber, or may be empty. For example, a chamber to be used to measure an optical characteristic value of an interfering substance may be empty, and a chamber to be used to detect a target substance may contain a reagent used for detection of the target substance in advance. If the concentration of the target substance is measured with optical measurement without use of a reagent, the chamber to be used to measure the target substance may not contain the reagent.

For example, as for containing a reagent beforehand, respective reagents may be contained in the form of dry reagents by applying them in portions 325a or 325b corresponding to the chambers of the top plate 320a or the bottom plate 320b, drying them, and then joining the top, middle, and bottom plates 320a, 320c, and 320b together in alignment with hole 325c. However, exemplary embodiments of the microfluidic device 300 are not limited thereto, and the reagents may also be contained in the liquid form or the bead form.

Once the sample is injected into the sample inlet hole 321 of the microfluidic device 300, the sample is moved to the chambers 200 along the channel 322. Once the sample is moved to the chambers 200, the test device 100 may measure the concentration of the target substance or interfering substance by irradiating light at a proper wavelength to each of the chambers 200 and detecting light transmitted through or reflected from the chamber. Operation of the test device for testing a sample contained in the cartridge typed microfluidic device will now be described.

Figure 5:
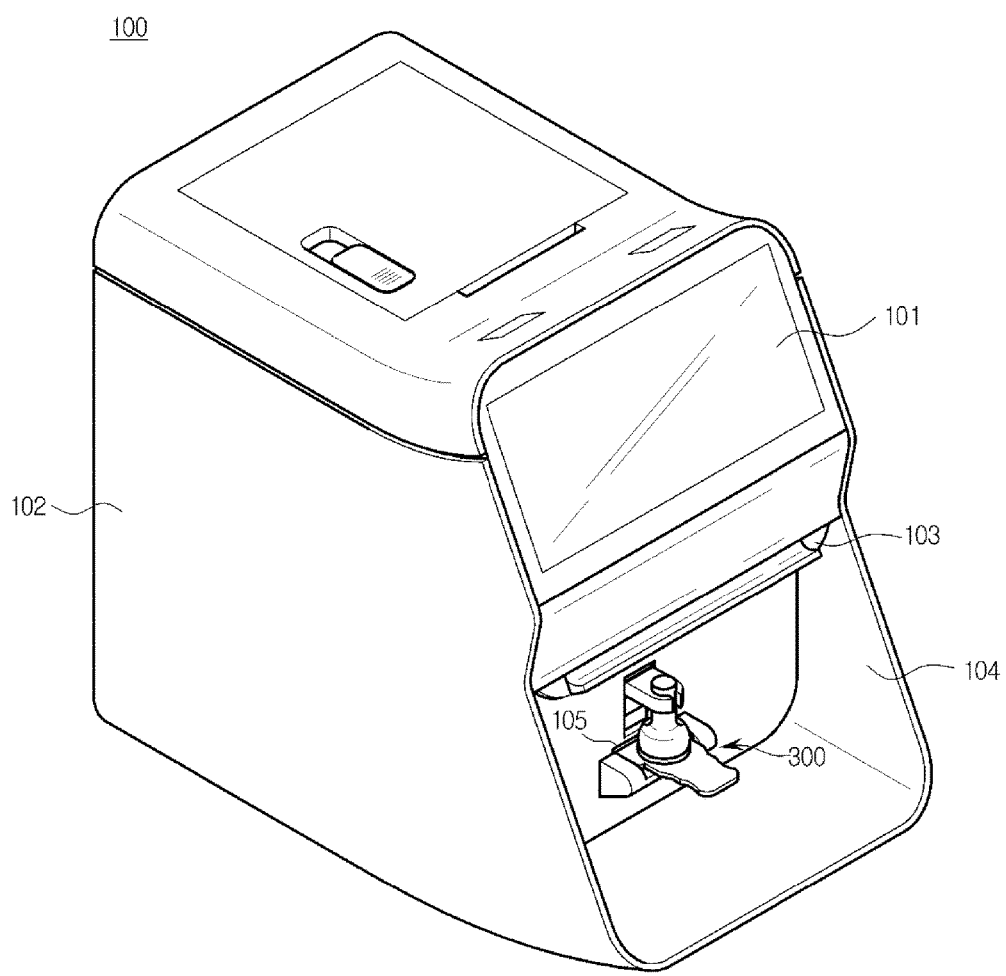
FIG. 5 is a view of appearance of a test device for testing a sample contained in a microfluidic device of a cartridge type.

FIG. 5 is a test device for testing a sample contained in a microfluidic device of a cartridge type.

Referring to FIG. 5, a mounting unit 104 is formed in a main body 102 that constitutes appearance of the test device 100. The mounting unit 104 is a space in which the microfluidic device 300 that contains a sample is mounted. The microfluidic device 300 may be mounted in the test device 100 after a door 103 slides open. Specifically, the platform 320 of the microfluidic device 300 may be inserted into a insertion groove 105 formed in the mounting unit 104.

After the mounting of the microfluidic device 300 is completed, the door 103 is closed and then a test begins. Optical characteristic values may be measured in the inside of the main body 102 with the platform 320 inserted, and the concentration or a diagnostic result of a measurement item determined by the data processor 130 may be displayed on the display 101.

Figure 6:
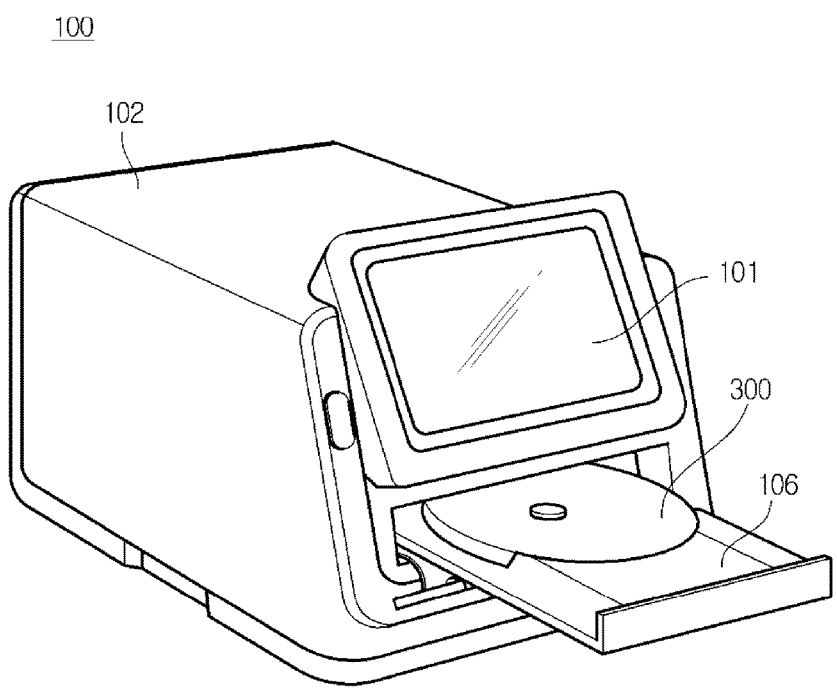
FIG. 6 is a view of appearance of a test device for testing a sample contained in a microfluidic device of a disc type.
Figure 7:
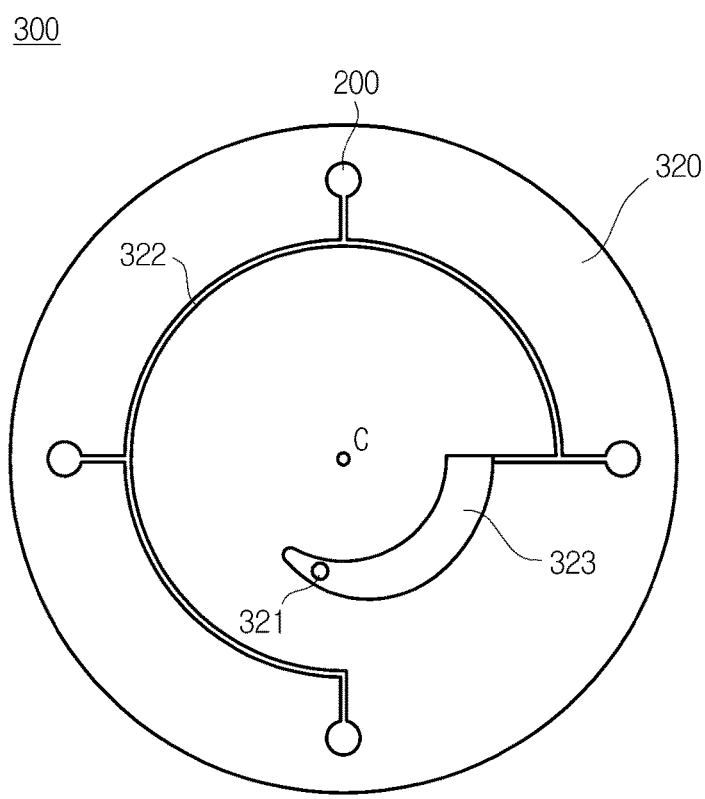
FIG. 7 shows a microfluidic device of a disc type, which may be mounted on the test device of FIG. 6.

FIG. 6 is a test device for testing a sample contained in a microfluidic device of a disc type, and FIG. 7 shows a microfluidic device of a disc type, which may be mounted in the test device of FIG. 6.

Referring to FIG. 6, the test device 100 in accordance with another exemplary embodiment may test a sample contained in the microfluidic device 300 of a disc type. When the sample is injected into the microfluidic device 300, and the microfluidic device 300 is settled on a tray 106 of the test device 100, the settled microfluidic device 300 is inserted to the inside of the main body 102 of the test device 100 with the tray 106.

Once the microfluidic device 300 is inserted, the test device 100 rotates the microfluidic device 300 about center C according to a predefined sequence, and the sample injected into the microfluidic device 300 is moved to the chambers 200 by a centrifugal force.

Optical characteristic values of the sample may be measured in the inside of the main body 102 with the platform 320 inserted, and the concentration or diagnostic result of a measurement item determined by the data processor 130 may be displayed on the display 101.

Referring to FIG. 7, the microfluidic device 300 of a disc type may include the platform 320 and microfluidic structures formed on the platform 320

The microfluidic structure may include a plurality of chambers that contain the sample or a reagent, and a channel that connects the chambers. The microfluidic structures are formed inside the platform 320, and in the exemplary embodiment, it is assumed that the platform 320 is formed of a transparent material, so the microfluidic structures formed inside the platform 320 are viewable when viewed from the top.

The platform may be easy to be molded and have the surface formed of a biologically inactive material, such as plastic like PMMA, PDMS, PC, PP, PVA, PE, etc., glass, mica, silica, silicon wafer, etc.

However, exemplary embodiments are not limited thereto, and any material that is chemically and biologically stable and mechanically porous may be used as a material for the platform 320. Plus, the platform 320 may further have optical transparency to optically analyze the test results in the microfluidic device 300.

The microfluidic device 300 of a disc type may move a substance within the microfluidic structure by a centrifugal force due to its rotation. While the platform 320 of a disc type is shown in the exemplary embodiment of FIG. 7, the platform 320 may also have the shape of a complete circle, a sector, or a polygon if it is rotatable.

On the platform 320, the sample inlet hole 321, a sample providing chamber 323 for containing a sample injected through the sample inlet hole 321 and providing the sample to other chambers 200, the channel 322 for connecting the chambers 200 and the sample providing chamber 323 for the injected sample to be moved to the chambers 200.

As for a blood sample, although not shown, a microfluidic structure for centrifugation may further be included in the microfluidic device 300 as needed, and even a metering chamber for moving a fixed amount of sample to the chambers 200, a buffer chamber for containing a buffer fluid, etc., may further be included.

The platform 320 may include multi-layered plates. For example, in a case that the platform 320 includes two plates, top and bottom plates, an engraved structure that corresponds to a microfluidic structure, such as a chamber or a channel may be formed on the plane where the top and bottom plates are in contact, and a space for containing fluids and a passage for the fluids to flow through may be provided in the inside of the platform 320 by joining the two plates. Connection between the plates may be made by various methods, such as adhesion with an adhesive or double-sided adhesive tape, or ultrasound joining, laser welding, etc.

The test device 100 and microfluidic device 300 mounted on the test device 100 as described above are merely examples, and exemplary embodiments are not limited thereto. Not only the microfluidic device 300 of the cartridge type or disc type but also cuvettes to contain the sample may be mounted on the test device 100. In this case, the chambers 200 are implemented in the cuvette type to be mounted on the test device 100. After the chamber 200 is mounted, optical characteristic values are measured, and a series of operations for measuring the concentration of total bilirubin present in the sample are performed as described above.

Figure 8:
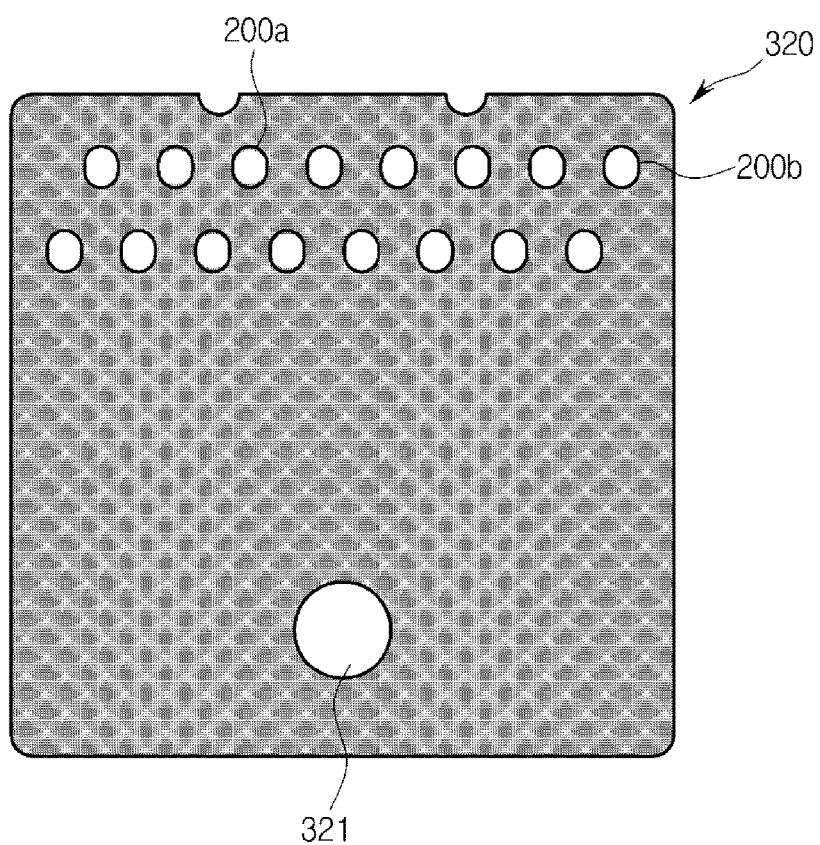
FIG. 8 shows chamber arrangement for performing a sample test method, according to an exemplary embodiment.
Figure 9:
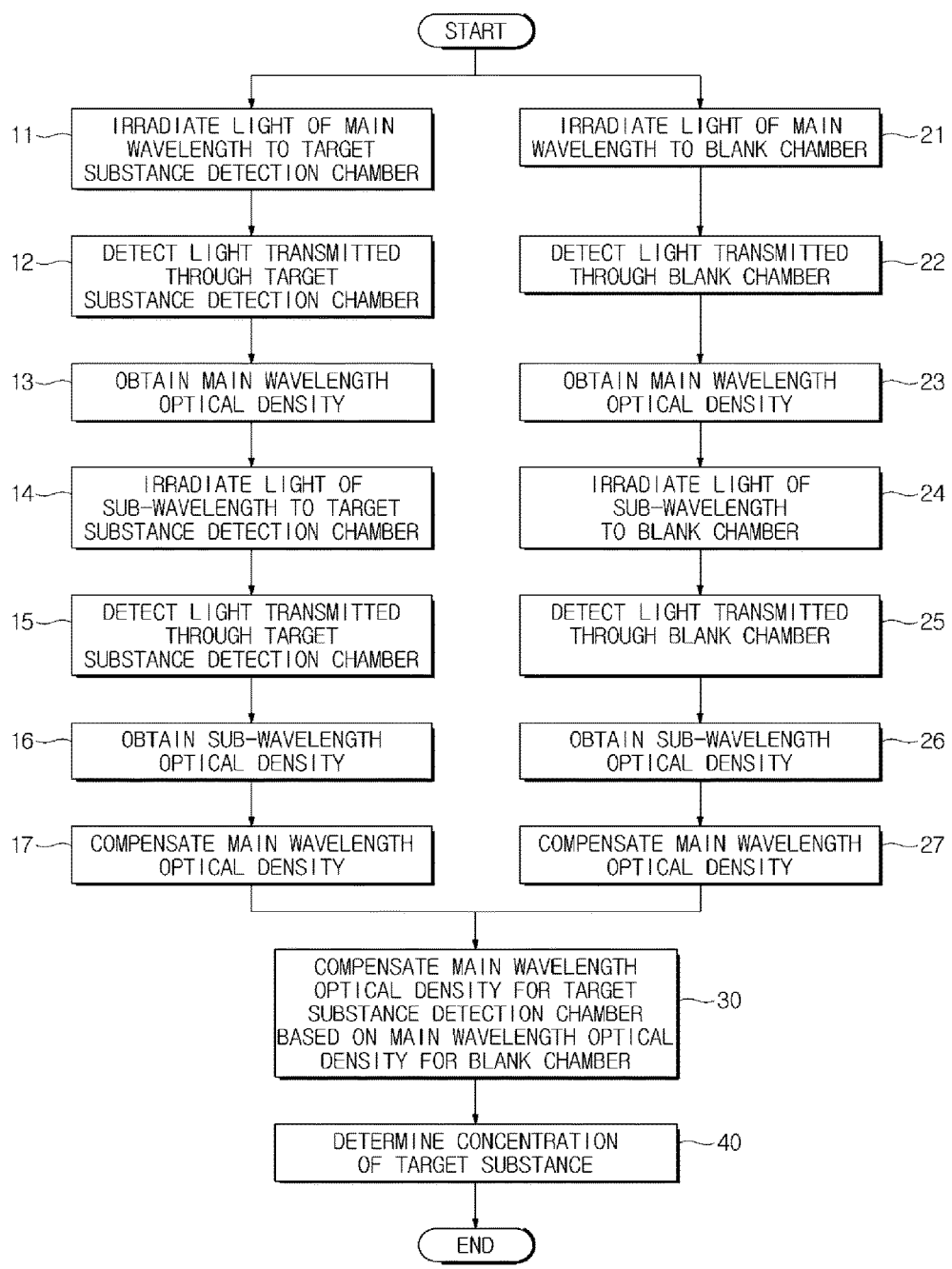
FIG. 9 is a detailed flowchart illustrating the sample test method of the exemplary embodiment shown in FIG. 1.

FIG. 8 shows chamber arrangement for performing a sample test method, according to an exemplary embodiment, and FIG. 9 is a detailed flowchart illustrating the sample test method of FIG. 1. In the exemplary embodiment of FIG. 8, it is assumed that the microfluidic device 300 of a cartridge type is used.

As discussed above, the test device 100 may measure optical characteristic values of a target substance or interfering substance by irradiating light to the chambers 200 formed in the microfluidic device 300 and performing detection. In the case of measuring the concentration of the target substance without use of a reagent, it is also possible to measure optical characteristic values of the target substance and interfering substance in the same chamber. On the other hand, if a reagent is used to measure the concentration of the target substance and the reagent influences measurement of an optical characteristic value of the interfering substance, optical characteristic values of the target substance and interfering substance may be measured in different chambers.

For this, as shown in FIG. 8, a chamber 200a among the plurality of chambers 200 may be used as a target substance detection chamber, and another chamber 200b may be used as a blank chamber for measuring an optical characteristic value of an interfering substance. A sample injected into the sample inlet hole 321 is moved both to the target substance detection chamber 200a and to the blank chamber 200b, and thus respective optical characteristic values of the target substance and interfering substance may be measured by irradiating light to each of the target substance detection chamber 200a and the blank chamber 200b and performing detection.

Operations 11 to 17 and 21 to 27 of FIG. 9 represent procedures of measuring optical characteristic values of the target substance and interfering substance in the sample test method of FIG. 1, respectively.

First, the procedure of measuring an optical characteristic value of the target substance will now be described. In the exemplary embodiment, it is assumed that the optical characteristic value is a measurement of optical density.

The light source 111 irradiates light of a main wavelength to the target substance detection chamber 200a, in operation 11. The target substance detection chamber 200a may contain a reagent for detecting the target substance and a sample, in which case an optical characteristic value due to a reaction between the reagent and the sample is measured. Alternatively, optical characteristics of the target substance itself contained in the sample may be measured without use of the reagent. The main wavelength refers to a wavelength specific to a substance to be detected, at which the substance has the highest optical density, or at which a product resulting from a reaction between the reagent and the substance has the highest optical density, or at which a product resulting from reaction catalyzed by the substance has the highest optical density.

The detector 112 detects light transmitted through the target substance detection chamber 200a, in operation 12.

Based on electric signals output from the detector 112, a main wavelength optical density of the target substance is obtained, in operation 13.

The light source 111 then irradiates light of a sub-wavelength to the target substance detection chamber 200a, in operation 14. The sub-wavelength refers to a wavelength used to compensate the main wavelength optical density.

The detector 112 detects light transmitted through the target substance detection chamber 200a, in operation 15.

Based on electric signals output from the detector 112, a sub-wavelength optical density of the target substance is obtained, in operation 16.

The main wavelength optical density is compensated using the obtained sub-wavelength optical density, in operation 17. For example, the main wavelength optical density may be compensated by subtracting the sub-wavelength optical density from the main wavelength optical density.

To measure an optical characteristic value of the interfering substance, the light source 111 irradiates light of a main wavelength to the blank chamber 200b, in operation 21. In this case, the blank chamber 200b does not contain a reagent.

The detector 112 detects light transmitted through the blank chamber 200b, in operation 22.

Based on electric signals output from the detector 112, a main wavelength optical density of the interfering substance is obtained, in operation 23.

The light source 111 then irradiates light of a sub-wavelength to the blank chamber 200b, in operation 24.

The detector 112 detects light transmitted through the blank chamber 200b, in operation 25.

Based on electric signals output from the detector 112, a sub-wavelength optical density of the interfering substance is obtained, in operation 26.

The main wavelength optical density is compensated using the obtained sub-wavelength optical density, in operation 27. For example, the main wavelength optical density may be compensated by subtracting the sub-wavelength optical density from the main wavelength optical density.

The optical density of the target substance may then be compensated by subtracting the optical density of the interfering substance to which a fluctuation coefficient is applied, from the optical density of the target substance, in operation 30.

The concentration of the target substance is then determined based on the compensated optical density of the target substance, in operation 40. With the compensated optical density from which interference of the interfering substance is eliminated, more accurate concentration may be determined.

To perform tests in accordance with the aforementioned sample test method in the test device 100, the data processor 130 may do compensation of the main wavelength optical density in operations 17, 27, and 30 and determination of the concentration of the target substance in operations 40.

The sample test method in accordance with an exemplary embodiment and operation of the test device for performing the method will now be described in more detail.

As discussed above, in measuring a GGT level of a blood sample, other substances present in the blood, especially, in the hemolytic blood may act as interfering substances. An example of a method for measuring the GGT level may use the hydrolysis of a synthetic substrate as represented in the following reaction formula 1:

L-γ-glutamyl-3-carboxyl-4-nitroanilide+Glycylglycine

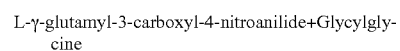

------>L-γ-glutamyl glycylglycine+5-amino-2-nitro-benzoic acid,     [Reaction Formula 1]

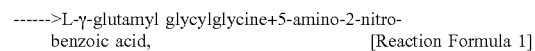

where, L-γ-glutamyl-3-carboxyl-4-nitroanilide is a synthetic substrate, which is hydrolyzed by active GGT into L-γ-glutamyl glycylglycine and 5-amino-2-nitro-benzoic acid. Glycylglycine is a substance to catalyze the hydrolysis of GGT. Reaction rate at which the synthetic substrate is hydrolyzed and metastasized by GGT may be measured by optically measuring the color of the hydrolysis derivative 5-amino-2-nitro-benzoic acid, and the GGT level may be determined from the reaction rate.

However, due to interference of other interfering substances present in the sample, such as hemoglobin or bilirubin, the amount of hydrolysis derivative may appear to be abnormally high, hampering accuracy and correlation of the measured GGT level. Accordingly, the sample test method and test device in accordance with an exemplary embodiment compensates the optical characteristic value of GGT for interference caused by the interfering substances.

Turning back to FIG. 8, the target substance detection chamber 200a contains a reagent for detecting GGT while the blank chamber 200b does not contain a reagent. The fact that the blank chamber 200b does not contain any reagent means that no reagent is contained to be used for detecting the interfering substance.

The reagent for detecting GGT may include a synthetic substrate L-γ-glutamyl glycylglycine and glycylglycine that catalyzes hydrolysis of the synthetic substrate, and further include stabilizers, buffers, surfactants, preservatives, antistripping agents, excipients, etc., as needed.

Main and sub-wavelengths used to measure the GGT level using reaction formula 1, and main and sub-wavelengths used to be irradiated to the blank chamber 200b and to measure an influence of the interfering substance may be chosen in the range of 300 nm to 900 nm.

Respective main and sub-wavelengths may be determined by experiments, theories, statistics, or simulations taking into account types of the target and interfering substances. Specifically, both main wavelengths of light to be irradiated to the target substance detection chamber 200a and to the blank chamber 200b may be chosen to be 405 nm. The sub-wavelengths to be irradiated to the target substance detection chamber 200a and the blank chamber 200b are chosen to be 450 nm and 810 nm, respectively.

To compensate the main wavelength optical density of GGT in operation 17, optical density obtained by irradiating light at 450 nm to the target substance detection chamber 200a is subtracted from optical density obtained by irradiating light at 405 nm.

In addition, to compensate the main wavelength optical density of the interfering substance in operation 27, optical density obtained by irradiating light at 810 nm to the blank chamber 200b is subtracted from optical density obtained by irradiating light at 405 nm.

It is also possible to omit compensation of the main wavelength optical density based on the sub-wavelength optical density. In other words, the procedure of irradiating light of respective sub-wavelengths to the target substance detection chamber 200a and blank chamber 200b, detecting light transmitted through the respective chambers, and then subtracting the sub-wavelength optical density from the main wavelength optical density may be omitted.

Optical density of the target substance may be compensated in operation 30 as represented in the following equation 1:

$$OD_{Eff} = OD_{tgt} - F \times OD_{int} \quad (1)$$

where $OD_{Eff}$ is an effective optical density, indicating an optical density for which the interference of the interfering substance is compensated. $OD_{tgt}$ is an optical density measured for the target substance, e.g., GGT, indicating the main wavelength optical density compensated in operation 17 of FIG. 9, and $OD_{int}$ is an optical density of the interfering substance indicating the main wavelength optical density compensated in operation 27. However, in a case that compensation of the main wavelength optical density based on the sub-wavelength optical density is omitted, it is natural that $OD_{tgt}$ may be the main wavelength optical density of the target substance, and $OD_{int}$ may be the main wavelength optical density of the interfering substance.

F is an effect of the interfering substance, e.g., a fluctuation coefficient indicating a degree to which the interference of the interfering substance influences measurement of the concentration of the target substance, which may be determined by experiments, theories, statistics, or simulations. As an example of the fluctuation coefficient obtained by an experiment, $1/70 \sim 1/50$ may be applied.

While a result from application of the fluctuation coefficient to the optical density of the interfering substance is eliminated from optical density measured for the target substance in equation 1, it is possible to add the result to the optical density measured for the target substance based on the interference of the interfering substance that influences the optical density of the target substance.

The concentration of the target substance is then determined based on the optical density for which the interference is compensated, in operation 40. A kinetic scheme may be applied for determination of the GGT level.

Figure 10:
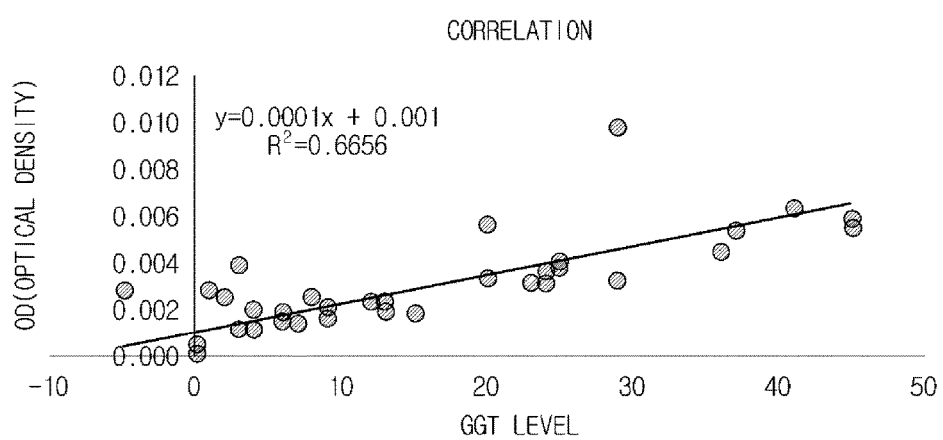
FIG. 10 shows a graph representing correlations of measurements of optical density of gamma-glutamyl transferase (GGT) without compensation for interference of an interfering substance.
Figure 11:
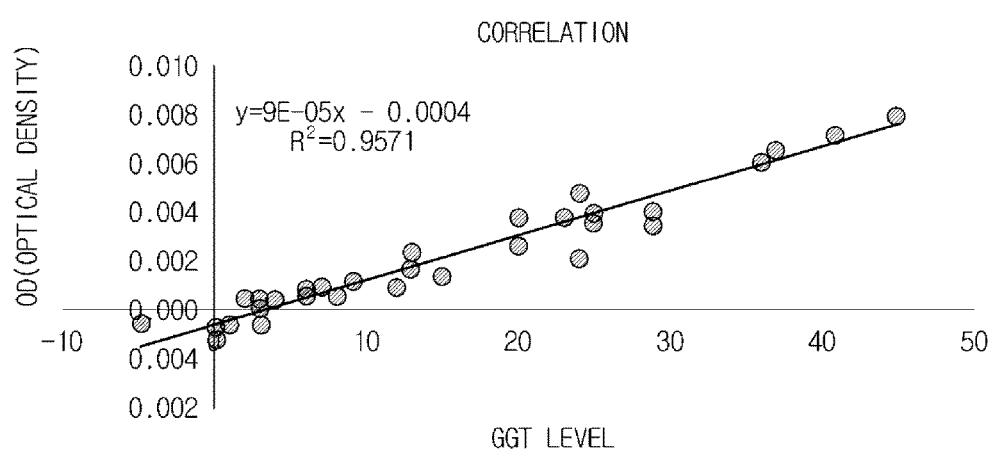
FIG. 11 shows a graph representing correlations of measurements of concentrations of GGT after compensation for interference of an interfering substance based on a sample test method and test device, according to an exemplary embodiment.

FIG. 10 shows a graph representing correlations of measurements of optical density of GGT without compensation for interference of an interfering substance, and FIG. 11 shows a graph representing correlations of measurements of GGT level with compensation for interference of interfering substances based on a sample test method and test device, according to an exemplary embodiment. Both graphs show measurements in a low concentration (GGT level) region below 50μ/L.

Correlation is an index indicating a correlation of test results between a device as a standard and a device subject to performance determination, and accuracy may be indirectly determined for the correlation. The correlation may be represented by correlation coefficient R, in which case the nearer to 1 the absolute value of the correlation coefficient R, the higher the accuracy.

In the graph of FIG. 10, the Y-axis represents optical densities for which interference of interfering substances is not compensated, and the X-axis represents GGT levels measured by the standard device. Referring to FIG. 10, where interference of interfering substances are not compensated for, the correlation coefficient R was determined to be 0.82.

In the graph of FIG. 11, the Y-axis represents optical densities for which interference of interfering substances is compensated for, and the X-axis represents GGT levels measured by the standard device. Referring to FIG. 11, where interference of interfering substances is compensated for by the sample test method and test device in accordance with an exemplary embodiment, the correlation coefficient R is determined to be 0.98, so it is seen that the correlation has improved as compared to an occasion where interference of interfering substances is not compensated for.

Figure 12:
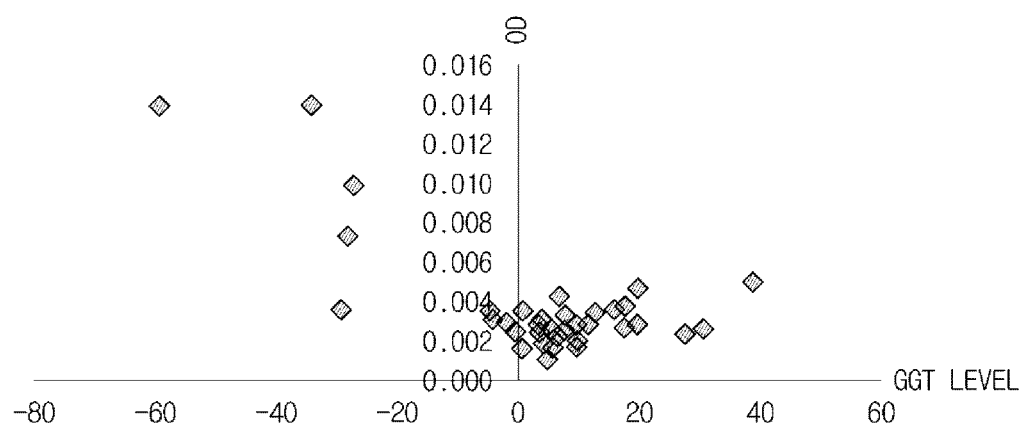
FIG. 12 shows a graph representing positive fallacy of measurements of optical density of GGT without compensation for interference of an interfering substance.
Figure 13:
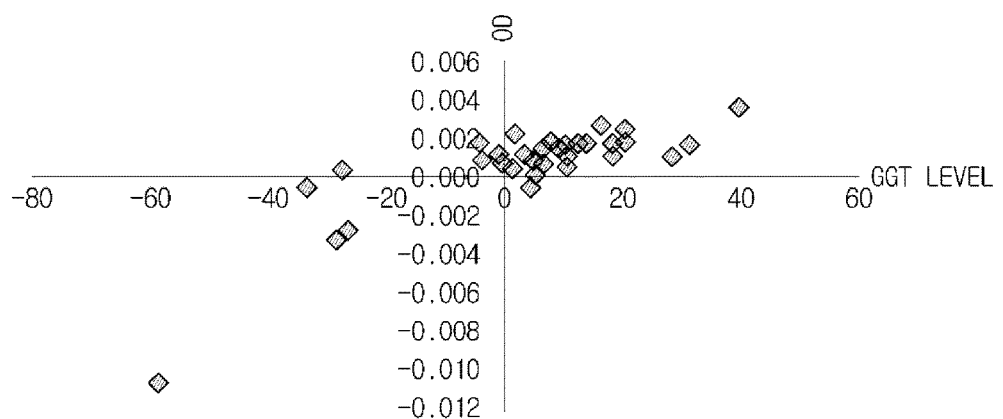
FIG. 13 shows improvements in positive fallacy after compensation for interference of an interfering substance based on a sample test method and test device, according to an exemplary embodiment.

FIG. 12 shows a graph illustrating positive fallacy of measurements of optical density of GGT without compensation for interference of interfering substances, and FIG. 13 shows improvements in positive fallacy with compensation for interference of interfering substances based on a sample test method and test device, according to an exemplary embodiment.

Measurements of optical densities of GGT without compensation for interference of interfering substances show that false positive appears in that optical densities in the negative concentration region are measured to be positive, as shown in FIG. 12.

On the other hand, measurements of optical densities of GGT with compensation for interference of interfering substances show that false positive is eliminated in that optical densities in the negative concentration region are measured to be negative, as shown in FIG. 13.

The aforementioned exemplary embodiments assume that the target substance is GGT and the interfering substance is hemoglobin, bilirubin, or the like, present in a blood sample, especially, in a hemolytic blood sample, but they are not limited thereto. Any other substance than GGT among all the substances present in the bio-sample may be the target substance, while other substances than hemoglobin or bilirubin may be the interfering substances. As long as proper main and sub-wavelengths are chosen depending on types of the target and interfering substances, the sample method and test device in accordance with the exemplary embodiments may be applied for other substances.

As discussed above, bilirubin present in blood may be a measurement item, or act as an interfering substance that influences measurement of other substances. To eliminate the bilirubin interference, it is required to accurately measure the concentration or an optical characteristic value of bilirubin present in the sample. In the following description, a method for measuring the concentration and optical characteristic value of bilirubin present in a blood sample will be discussed first, and then a method for compensating for the bilirubin interference will be discussed.

Figure 14:
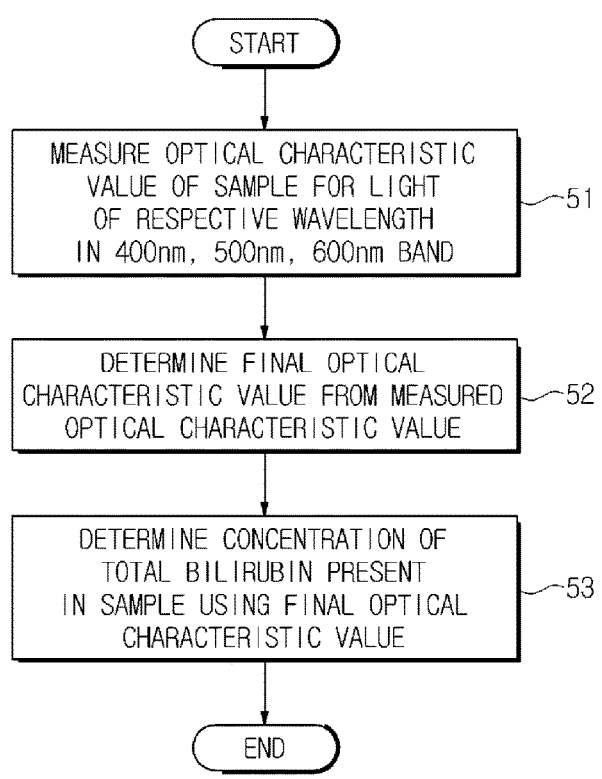
FIG. 14 is a flowchart illustrating the measurement of a concentration of bilirubin in a test method, according to an exemplary embodiment.

FIG. 14 is a flowchart illustrating the measurement of a concentration of bilirubin in a test method, according to an exemplary embodiment.

Referring to FIG. 14, optical characteristic values of a sample are measured for light of respective wavelengths in 400 nm, 500 nm, and 600 nm bands, in operation 51. One skilled in the art would understand that a range of a band spans approximately 100 nm to distinguish effects of the wavelength on different substances.

It is assumed that the sample contains bilirubin, and the optical characteristic values may be measured while the sample is contained in a chamber. Various optical characteristic values, such as optical density, reflectivity, transmittance, etc., may be measured. For convenience of explanation, however, it is assumed in the following exemplary embodiments that optical density is to be measured.

A final optical characteristic value is determined from the measured optical characteristic value, in operation 52.

The final optical characteristic value may be determined as represented in equation 2:

$$OD_F = OD_{400} - OD_{500} - OD_{600} \quad (2)$$

In equation 2, $OD_F$ represents a final optical density, $OD_{400}$ represents an optical density at a wavelength in the 400 nm band, $OD_{500}$ represents an optical density at a wavelength in the 500 nm band, and $OD_{600}$ represents an optical density at a wavelength in the 600 nm band.

Bilirubin mainly absorbs light of the 400 nm band, but its optical characteristic values may be measured at wavelengths even in the 500 nm and 600 nm bands, and the concentration of bilirubin may be more accurately determined by eliminating optical characteristic values measured at wavelengths in the 500 nm and 600 nm bands from an optical characteristic value measured at a wavelength in the 400 nm band.

It is also possible to perform compensation based on a sub-wavelength to further improve accuracy in the determined concentration. For this, an optical characteristic value may be measured even in the 800 nm band of sub-wavelength, especially, at 810 nm. After elimination of the optical characteristic value measured in the 800 nm band from the respective optical characteristic values measured in the 400 nm, 500 nm, and 600 nm bands, operation as represented in equation 2 may be performed. In this case, equation 2 may be expressed as in equation 3:

$$OD_F = (OD_{400} - OD_{800}) - (OD_{500} - OD_{800}) - (OD_{600} - OD_{800}) \quad (3)$$

With the determined final optical characteristic value, the concentration of total bilirubin present in the sample is determined, in operation 53.

To determine the concentration of bilirubin with the optical characteristic value, a calibration curve that represents relations between optical characteristic values and concentrations of a substance to be measured is pre-stored, and the concentration of the substance to be measured may be obtained by applying the optical characteristic value onto the calibration curve. Accordingly, even in this phase, the concentration of total bilirubin may be determined by applying the final optical density onto the pre-stored calibration curve for bilirubin.

In case a reagent is used to measure the concentration of a substance, even the same type of reagent has different characteristics every time it is manufactured, and accordingly, coefficients of the calibration curve may vary. In accordance with an exemplary embodiment of the sample test method, however, because no reagent is used to measure the concentration of bilirubin, the same calibration coefficient may still be applied.

Figure 15:
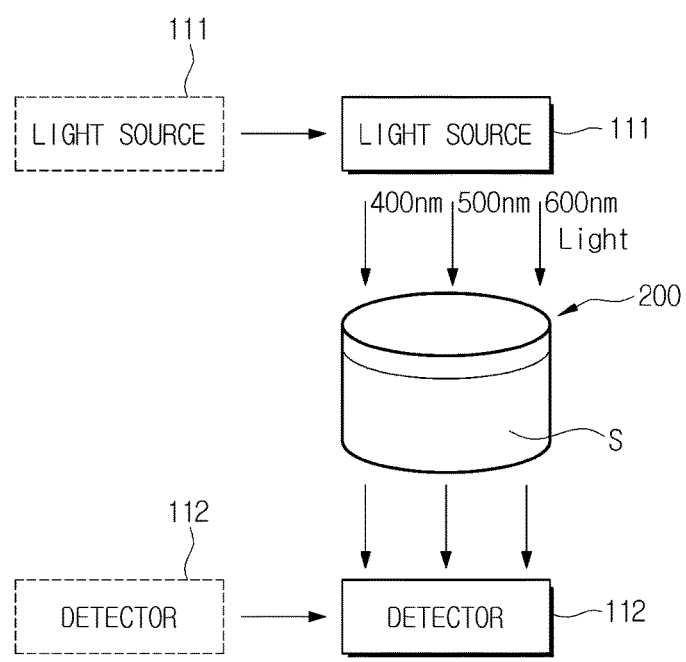
FIGS. 15 and 16 show operations of a test device measuring optical characteristic values of a sample contained in a chamber, according to an exemplary embodiment.
Figure 16:
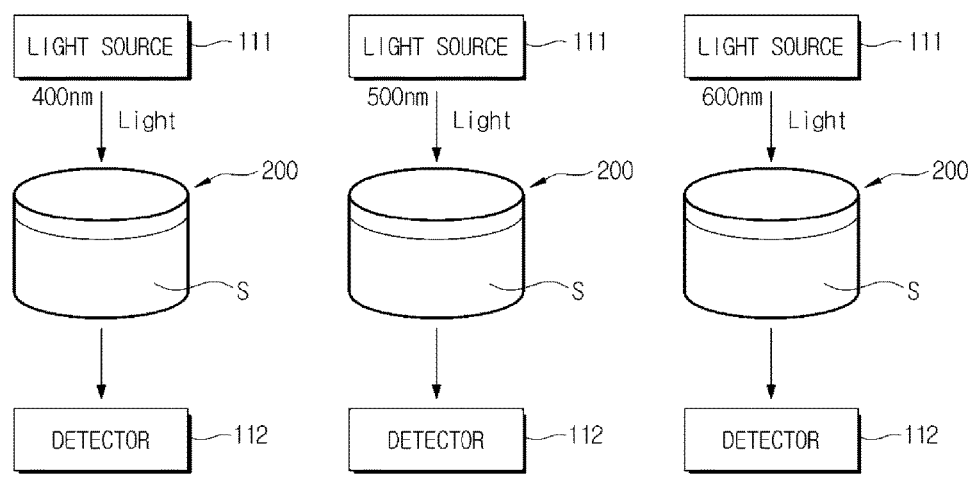

FIGS. 15 and 16 show operations of a test device measuring optical characteristic values of a sample contained in a chamber, according to an exemplary embodiment.

After the microfluidic device 300 is mounted on the test device 100, when a sample S is moved to the chamber 200 through the channel 322, or when the chamber 200 of a cuvette type that contains the sample S is mounted on the test device 100, the light source 111 irradiates light of wavelengths in the 400 nm, 500 nm, and 600 nm bands to the chamber 200 to measure the concentration of bilirubin present in the sample S.

In a case initial positions of the light source 111 and the detector 112 do not correspond to a position of the chamber 200, as shown in FIG. 15, the controller 120 may move the positions of the light source 111 and the detector 112 to positions corresponding to the chamber 200.

The light source 111 may include a plurality of light source elements to simultaneously irradiate light of wavelengths in the 400 nm, 500 nm, and 600 nm bands.

On the other hand, as shown in FIG. 16, the light source 111 may irradiate light of wavelengths in the 400 nm, 500 nm, and 600 nm bands with time differences.

The detector 112 detects light transmitted through the chamber 200, converts the detected light to an optical density corresponding to the light intensity, and outputs the optical density to the data processor 130. Alternatively, the data processor 130 may convert an electric signal output from the detector 112 to an optical density. The data processor 130 may then determine the concentration of total bilirubin by determining the final optical density with optical densities of respective wavelengths based on equation 2 and applying the final optical density onto the pre-stored calibration curve.

The display 101 may display the determined concentration, and a series of operations to measure the optical density and display the determined concentration may be controlled by the controller 120.

Operation of the data processor 130 to determine the concentration of total bilirubin based on the measured optical characteristic values will now be described in detail.

For example, it is assumed that the measurer 110 measured optical densities for light of wavelengths at 450 nm, 535 nm, and 630 nm, and that the results are as represented in the following table 1.

TABLE 1

|  | at 450 nm | at 535 nm | at 630 nm |
| --- | --- | --- | --- |
| Optical Density | 0.103 | 0.072 | 0.062 |

The data processor 130 determines the final optical density ODF by applying a measured optical density into equation 2, which becomes $OD_F=0.103-0.072-0.062=0.09$.

The final optical density $OD_F=0.09$ is applied onto the calibration curve. For example, if the calibration curve is represented in equation $y=-2824.5x^3+189.48x^2+88.078x+3.1558$, the final optical density 0.09 is applied to x, and accordingly, y=10.39. Accordingly, the concentration of total bilirubin present in the sample may be determined to be 10.39 mg/dL, and the controller 120 may provide the result for the user by displaying the result on the display 101.

In the meantime, there is an occasion when the purpose of the sample test is not to measure the concentration of total bilirubin present in the sample. For example, bilirubin present in the sample may act as an interfering substance in measuring one of electrolyte test items, a blood-chloride level.

Figure 17:
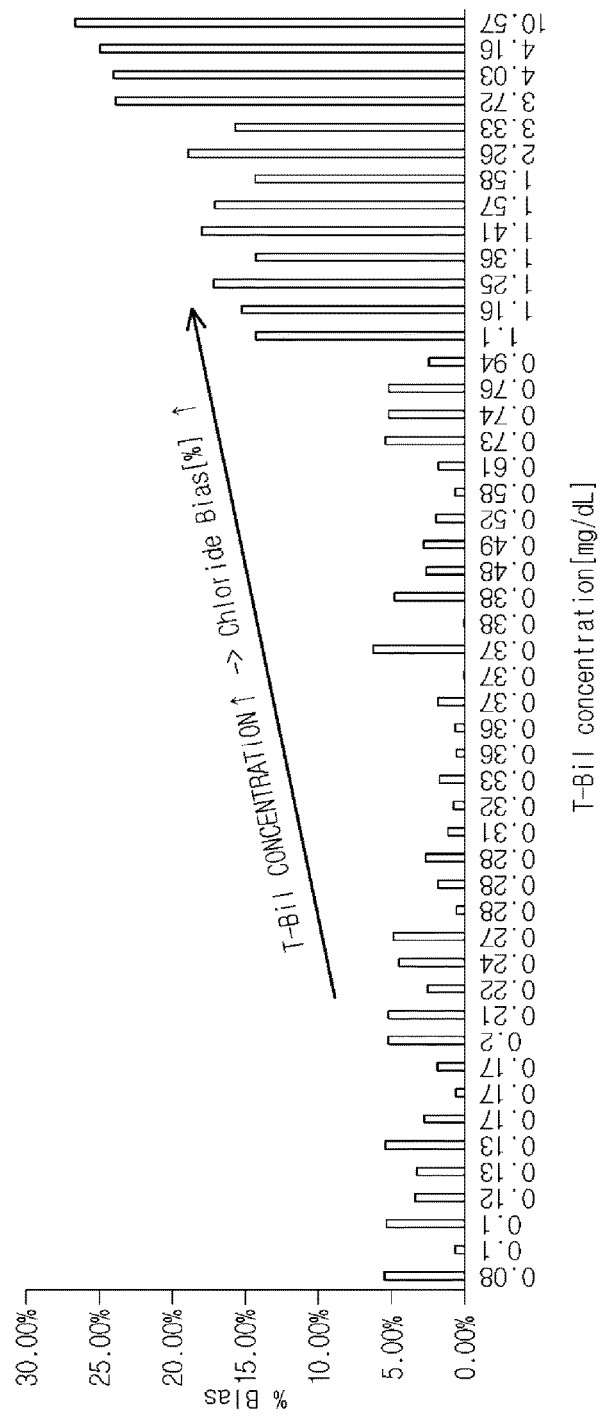
FIG. 17 shows a graph representing effects of bilirubin on measurements of the concentration of chloride.

FIG. 17 shows a graph representing effects of bilirubin on measurements of the concentration of chloride.

The concentration of chloride present in the sample is measured at different total bilirubin concentrations. A graph that represents differences (Bias) between actual concentration and measured concentration of chloride present in the sample at different concentrations of total bilirubin T-Bil is the graph shown in FIG. 10.

Referring to FIG. 17, the graph shows that the higher the concentration of total bilirubin present in the sample, the larger the difference (Bias) between actual concentration and measured concentration of chloride. Accordingly, with a substance other than bilirubin as a measurement item, it is necessary to effectively eliminate the effect of bilirubin that influences the measurement result. A sample test method for eliminating bilirubin interference will now be described.

Figure 18:
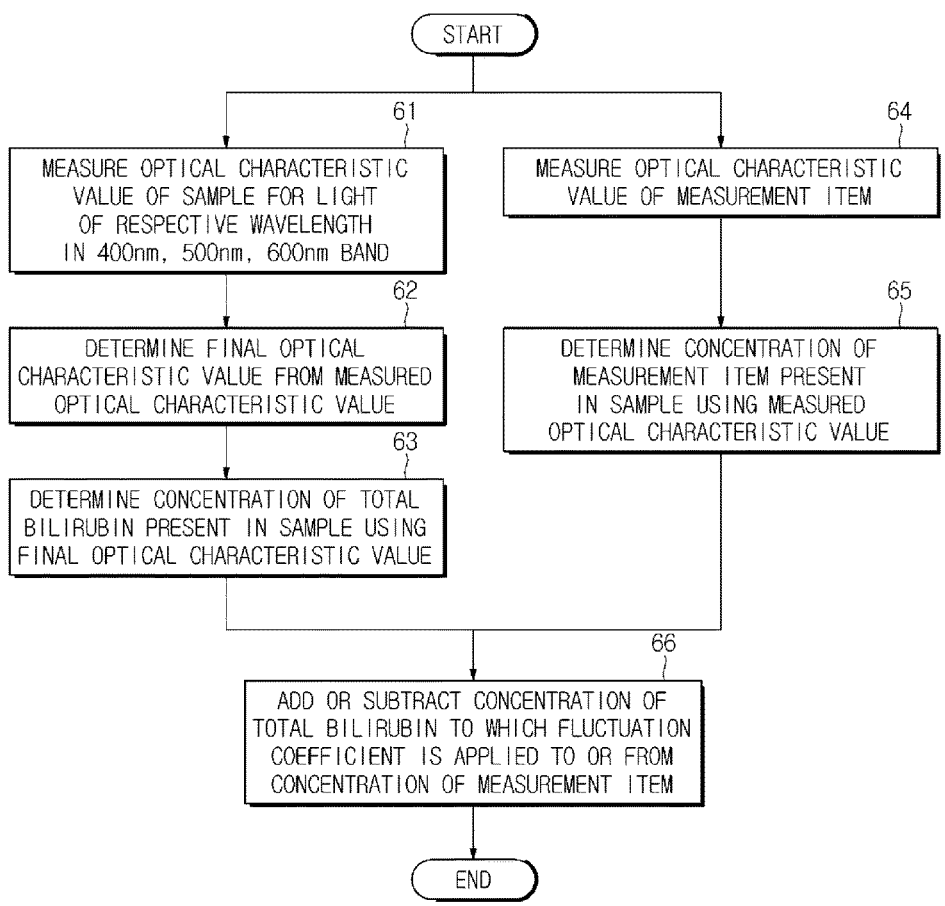
FIG. 18 is a flowchart illustrating elimination of bilirubin interference in a sample test method, according to an exemplary embodiment.

FIG. 18 is a flowchart illustrating elimination of bilirubin interference in a sample test method, according to an exemplary embodiment.

In the sample test method in accordance with the exemplary embodiment, the concentration of total bilirubin measured by employing an optical scheme without adding a diluted solution to the sample or adding a separate reagent for measurement of bilirubin may be used to eliminate the bilirubin interference.

Referring to FIG. 18, respective optical characteristic values of a sample are measured for light having wavelengths in the 400 nm, 500 nm, and 600 nm bands, in operation 61, and a final optical characteristic value may be determined from the measured optical characteristic values, in operation 62. With application of the determined final optical characteristic value onto the calibration curve, the concentration of total bilirubin present in the sample is determined, in operation 63. Those operations are the same as operations 51 to 53 of FIG. 14, so the detailed description will be omitted herein.

The concentration of a measurement item may be determined at the same time as, or regardless of, or subsequently to determination of the concentration of total bilirubin. For this, optical characteristic values of the measurement item are measured in operation 64, and the concentration of the measurement item present in the sample may be determined using the measured optical characteristic values in operation 65.

Wavelengths of light used to measure optical characteristic values of the measurement item may vary by the type of the measurement item, and at this time, a reagent may also be used to detect the measurement item. In determining the concentration of the measurement item using the measured optical characteristic values, the calibration curve pre-stored for the measurement item may be used.

A fluctuation coefficient is applied for the determined concentration of total bilirubin, and the result is added to or subtracted from the concentration of the measurement item, in operation 66. The concentration of the measurement item is the concentration determined in operation 65. This procedure may be represented in equation 4:

$$C_{Eff}=C_{tgt}\pm F\times C_{T\_Bil}, \quad (4)$$

where $C_{Eff}$ refers to an effective concentration of the target substance, resulting from compensation for the bilirubin interference. $C_{tgt}$ refers to the concentration of the target substance without elimination of the bilirubin interference, F refers to a fluctuation coefficient, and $C_{T\_Bil}$ refers to the concentration of total bilirubin determined in operation 63.

The fluctuation coefficient is a value indicating a degree to which bilirubin influences a measurement of the target substance, e.g., the concentration of the target substance. It may vary depending on measurement scheme, type of the target substance, length of the light path, measurement time, etc., and a proper fluctuation coefficient may be set in advance for each case. The proper fluctuation coefficient may be set by experiments, statistics, theories, or simulations.

The concentration of the target substance may be measured to be higher or less than its true concentration due to the bilirubin interference. In the former case, the concentration of total bilirubin to which the fluctuation coefficient is applied ($F\times C_{T\_Bil}$) is added to the concentration of the target substance ($C_{tgt}$), and in the latter case, the concentration of total bilirubin to which the fluctuation coefficient is applied ($F\times C_{T\_Bil}$) is subtracted from the measured concentration of the target substance ($C_{tgt}$), thereby determining the effective concentration of the target substance ($C_{Eff}$).

The sample test method in accordance with the exemplary embodiment eliminates the bilirubin interference based on the concentration. However, as discussed above, the bilirubin interference may also be eliminated based on optical characteristic values, as will be described below in detail.

Figure 19:
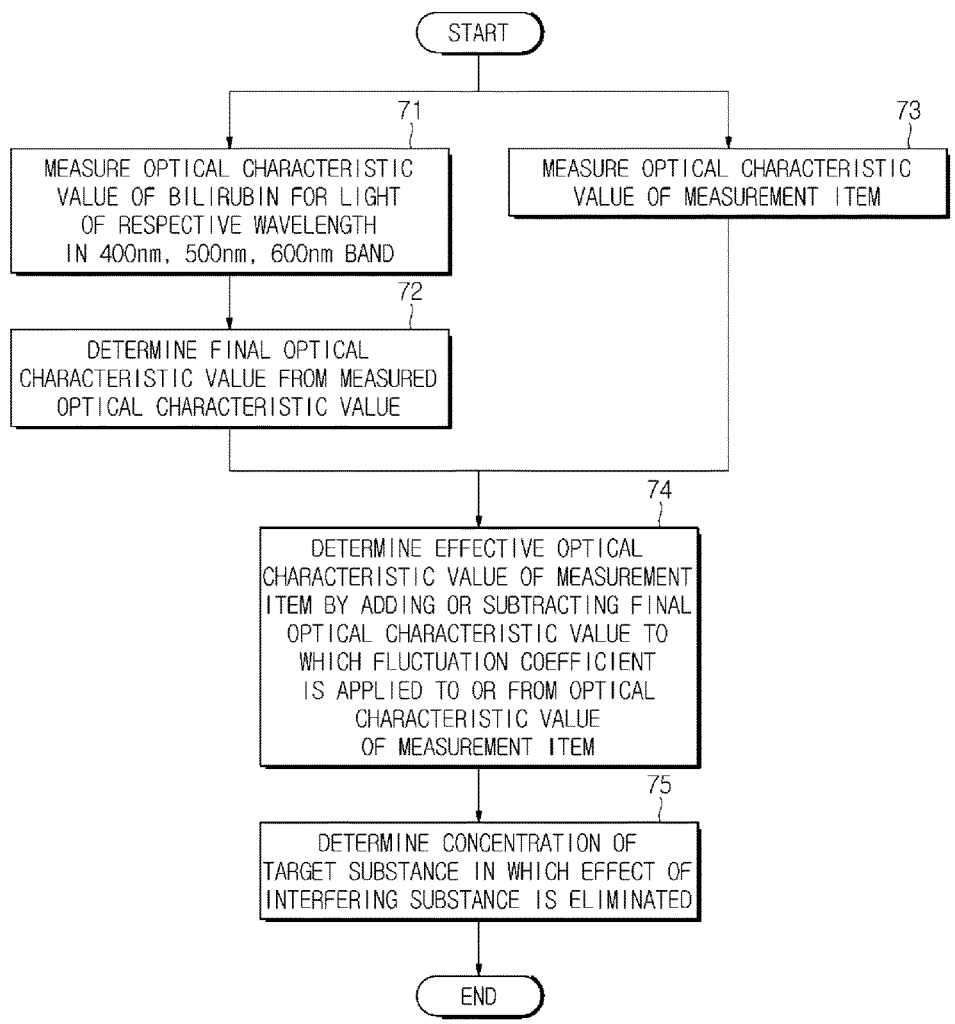
FIG. 19 is a flowchart illustrating elimination of bilirubin interference in a sample test method, according to another exemplary embodiment.

FIG. 19 is a flowchart illustrating elimination of bilirubin interference in a sample test method, according to another exemplary embodiment.

Referring to FIG. 19, respective optical characteristic values of a sample are measured for light of wavelengths in the 400 nm, 500 nm, and 600 nm bands, in operation 71, and a final optical characteristic value may be determined from the measured optical characteristic values, in operation 72. Those operations are the same as operations 51 and 52 of FIG. 14, so the detailed description will be omitted herein.

At the same time as, or regardless of, or subsequently to measurement of the optical characteristic value of the sample for bilirubin in operation 71, optical characteristic values of the sample for a measurement item are measured, in operation 73. Wavelengths of light used herein may vary by the type of the measurement item, and the optical characteristic values to be measured are assumed to be in the same type as that of the optical characteristic values measured in operation 71. In other words, if an optical density is measured in operation 71, an optical density is measured in operation 73 as well.

An effective optical characteristic value of the measurement item is determined by adding or subtracting the final optical characteristic value to which the fluctuation coefficient is applied to or from an optical characteristic value of the measurement item, in operation 74. This procedure may be represented in equation 5, and in the present example, optical density (OD) is used as an optical characteristic value.

$$OD_{Eff} = OD_{tgt} \pm F \times OD_{int}, \quad (5)$$

where $OD_{Eff}$ refers to an effective optical density of the target substance, resulting from elimination of the bilirubin interference. $OD_{tgt}$ refers to an optical density measured for the target substance, without elimination of bilirubin interference. The optical density is the one measured in operation 73. F is a fluctuation coefficient, and $OD_{int}$ is a final optical density of bilirubin that acts as an interfering substance, e.g., the final optical density $OD_F$ determined in operation 72.

The fluctuation coefficient F used in equation 5 may be different from that used in equation 4. The bilirubin interference is eliminated based on concentrations in the exemplary embodiment of FIG. 18, and on optical characteristic values in the exemplary embodiment of FIG. 19. These two exemplary embodiments is distinguished by their respective phases in which the bilirubin interference is eliminated, and since degrees to which bilirubin influences the concentration of the target substance and the optical characteristic value measured for the target substance may be different, respective fluctuation coefficients in the two exemplary embodiments may be different as well.

The optical density of the target substance may be measured to be higher or less than its true optical density due to the bilirubin interference. Therefore, taking into account such relations, it may be determined whether $F \times OD_F$ is to be added or subtracted to or from the optical density measured for the target substance ($OD_M$).

The concentration of the target substance from which the bilirubin interference is eliminated is determined using the effective optical characteristic value of the target substance, in operation 75. A calibration curve even for the target substance as a measurement item may be pre-stored, and the concentration of the target substance from which the bilirubin interference is eliminated may be determined by applying the effective optical density onto the pre-stored calibration curve.

It is natural to use the aforementioned test device 100 and microfluidic device 300 in performing the sample test method in accordance with exemplary embodiments of FIGS. 18 and 19. Turning back to FIG. 8, a reagent for measuring the concentration of the target substance is contained in the target substance detection chamber 200a. An optical characteristic value of bilirubin may be measured using the blank chamber 200b, or optical characteristic values of both the target substance and bilirubin may be measured using the target substance detection chamber 200a. It will be described below in more detail.

Specifically, a reaction between a reagent and a sample may be used to measure the concentration of a target substance. In case that the reagent does not influence bilirubin, the target substance detection chamber 200a may contain the reagent and optical characteristic values of both the target substance and bilirubin may be measured in the same chamber 200a.

Figure 20:
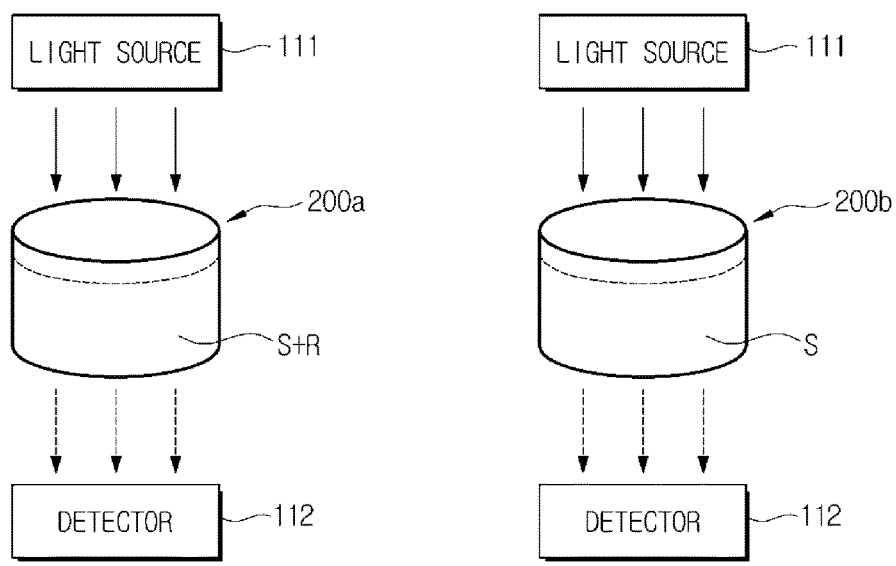
FIG. 20 shows operations of measuring optical characteristics of a target substance and bilirubin in different chambers.

FIG. 20 shows operations of measuring optical characteristics of a target substance and bilirubin in different chambers.

In a case a reagent for measuring the concentration of a target substance influences bilirubin, the target substance detection chamber 200a for measuring the concentration of the target substance and the blank chamber 20b for measuring the concentration of bilirubin may be separately prepared, as shown in FIG. 20.

With the reagent R used for detection of the target substance contained in the target substance detection chamber 200a, when the sample S is injected into the target substance detection chamber 200a, the light source 111 irradiates light of a proper wavelength for the target substance to the target substance detection chamber 200a, and the detector 112 detects light transmitted through the target substance detection chamber 200a and converts it to an optical characteristic value ($OD_{tgt}$) corresponding to the intensity of the detected light.

The blank chamber 200b does not contain any reagent for measuring the concentration of bilirubin but plasma may be added in the blank chamber 200b. When the sample S is injected into the blank chamber 200b, the light source 111 irradiates light of 400 nm, 500 nm, and 600 nm bands, and the detector 112 detects light transmitted through the blank chamber 200b and convert them to optical characteristic values ($OD_{400}$, $OD_{500}$, $OD_{600}$) corresponding to the intensity of the detected light. It is also possible to further irradiate and detect light of a sub-wavelength in the 800 nm band.

The optical characteristic values of the target substance and bilirubin may be measured at the same time, or with time differences, depending on the structure of the measurer 110.

Figure 21:
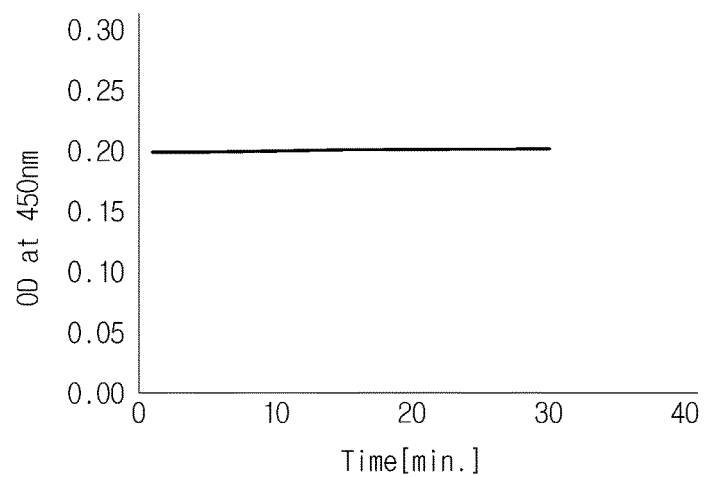
FIG. 21 shows a graph representing an optical density measured by a test device at 450 nm, according to an exemplary embodiment.
Figure 22:
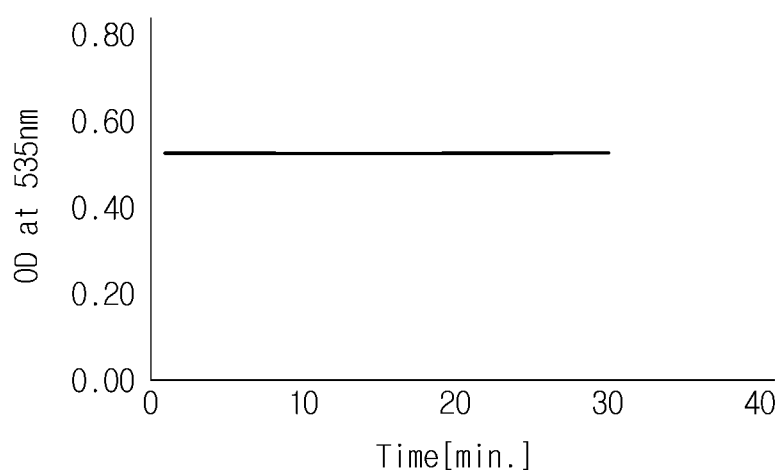
FIG. 22 shows a graph representing an optical density measured by a test device at 535 nm, according to an exemplary embodiment.
Figure 23:
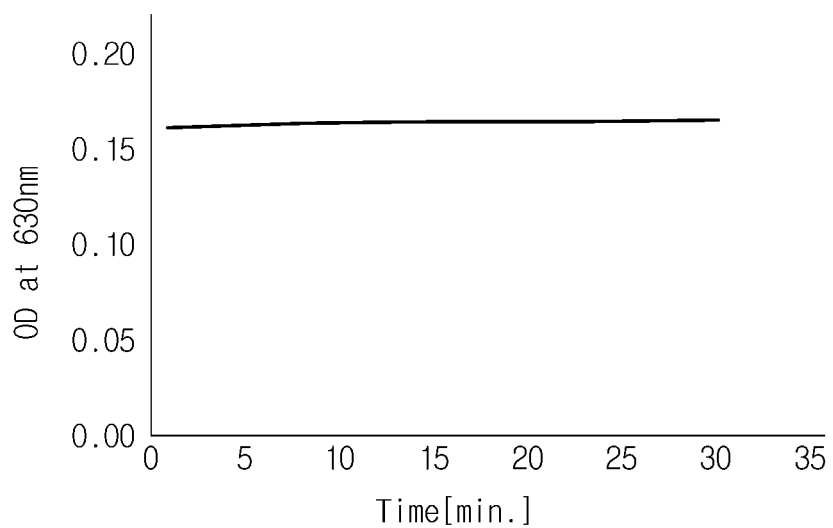
FIG. 23 shows a graph representing an optical density measured by a test device at 630 nm, according to an exemplary embodiment.

FIG. 21 shows a graph representing an optical density measured by a test device at 450 nm, according to an exemplary embodiment, FIG. 22 shows a graph representing an optical density measured by a test device at 535 nm, according to an exemplary embodiment, and FIG. 23 shows a graph representing an optical density measured by a test device at 630 nm, according to an exemplary embodiment.

With the test device 100, the concentration of bilirubin may be measured by optical measurement without use of a reagent. Results of measuring respective optical densities of a sample that does not react with a reagent at 450 nm, 535 nm, and 630 nm show that the measurements of the optical densities change little in time but remain as stable values, as shown in FIGS. 21 to 23.

Accordingly, since almost the same values may be obtained no matter what point of time the optical density is measured, the optical density is said not to be restricted by time.

Figure 24:
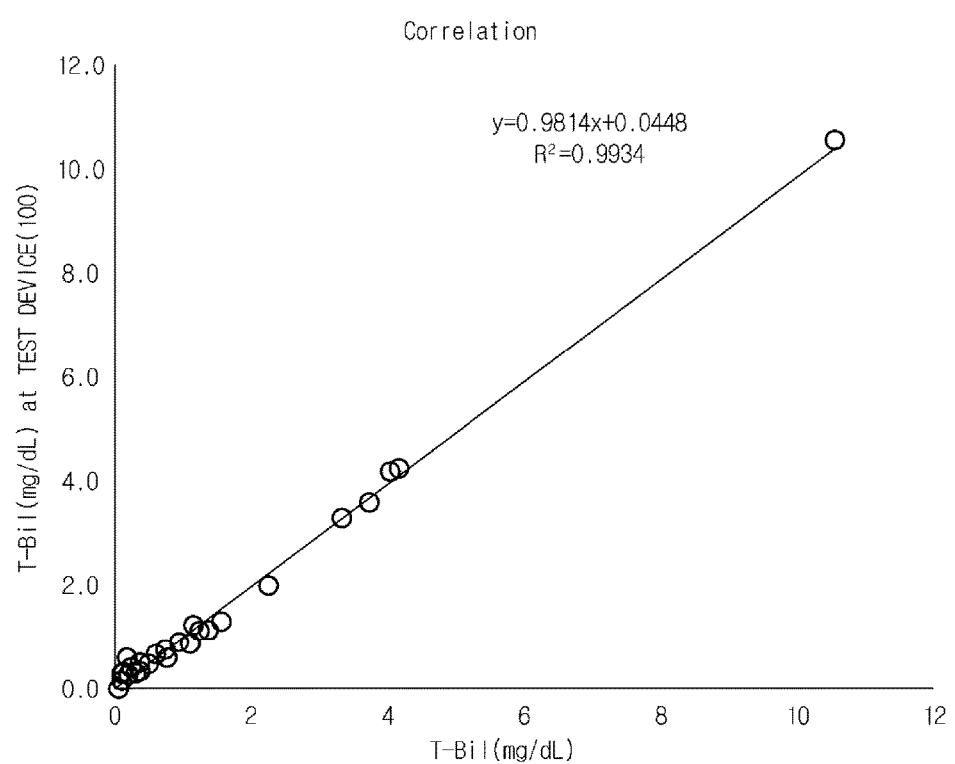
FIG. 24 shows a graph representing correlations of test results by a test device, according to an exemplary embodiment.

FIG. 24 shows a graph representing correlations of test results by a test device, according to an exemplary embodiment.

In the graph of FIG. 24, the Y-axis represents concentrations (mg/dL) of total bilirubin determined by the test device 100 in accordance with an exemplary embodiment, and the X-axis represents concentrations (mg/dL) of total bilirubin determined by a standard device.

Referring to FIG. 24, correlation coefficient R is determined to be 0.9967 ($R^2 = 0.09934$), which is very close to 1, meaning that accuracy of the test device 100 in accordance with the exemplary embodiment is very high.

FIG. 25 is a table representing respective concentrations of chloride and total bilirubin measured by a test device of an exemplary embodiment and a standard device.

In this regard, seven kinds of samples (samples A to G) including bilirubin and chloride were tested by each of the standard device and the test device 100 of the exemplary embodiment. Results of testing sample A show that the concentration of chloride was measured to be 89 mg/dL by the standard device, and the concentration of chloride before compensation for bilirubin interference was measured to be 116 mg/dL by the test device 100. The concentration of chloride before compensation for bilirubin interference corresponds to $C_{tgt}$ of equation 4.

Results of testing sample B show that the concentration of chloride was measured to be 92 mg/dL by the standard device, and the concentration of chloride before compensation for bilirubin interference was measured to be 104 mg/dL by the test device 100.

Results of testing sample C show that the concentration of chloride was measured to be 98 mg/dL by the standard device, and the concentration of chloride before compensation for bilirubin interference was measured to be 110 mg/dL by the test device 100.

Results of testing sample D show that the concentration of chloride was measured to be 106 mg/dL by the standard device, and the concentration of chloride before compensation for bilirubin interference was measured to be 112 mg/dL by the test device 100.

Results of testing sample E show that the concentration of chloride was measured to be 85 mg/dL by the standard device, and the concentration of chloride before compensation for bilirubin interference was measured to be 91 mg/dL by the test device 100.

Results of testing sample F show that the concentration of chloride was measured to be 85 mg/dL by the standard device, and the concentration of chloride before compensation for bilirubin interference was measured to be 91 mg/dL by the test device 100.

Results of testing sample G show that the concentration of chloride was measured to be 89 mg/dL by the standard device, and the concentration of chloride before compensation for bilirubin interference was measured to be 98 mg/dL by the test device 100.

In comparison of concentrations of chloride in the standard device and the test device (before compensation for the bilirubin interference), it is seen that there is a rather big difference between the concentrations and that the concentration of chloride is measured to be higher than its true concentration due to the bilirubin interference. Accordingly, it is seen that $F \times C_{T\_Bil}$ is to be subtracted from $C_{tgt}$ in compensating for the bilirubin interference in accordance with equation 4.

Referring again to FIG. 25, the concentrations of total bilirubin present in the respective samples were measured. For this, the test device 100 performed a series of operations 61 to 63 of FIG. 18, and the measured concentration of total bilirubin corresponds to $C_{T\_Bil}$ of equation 4.

The test device 100 determined the effective concentration of chloride $C_{Eff}$ by compensating for the bilirubin interference according to equation 4. The effective concentrations for samples A to G are 95 mg/dL, 96 mg/dL, 102 mg/dL, 107 mg/dL, 84 mg/dL, 88 mg/dL, and 95 mg/dL, respectively.

The difference (Bias) between the concentration measured by the standard device and the concentration $C_{tgt}$ measured by the test device 100 before compensation for the bilirubin interference is 30.30%, 13.10%, 12.20%, 5.60%, 7.20%, 7.20%, and 10.30% for samples A to G, respectively.

On the other hand, the difference (Bias) between the concentration measured by the standard device and the concentration $C_{Eff}$ measured by the test device 100 after compensation for the bilirubin interference is 7.00%, 4.20%, 3.90%, 1.40%, 0.80%, 3.50%, and 6.70% for samples A to G, respectively. It is seen that compensation for the bilirubin interference in the test device 100 significantly reduces the gap in concentration from the concentration measured by the standard device.

Figure 26:
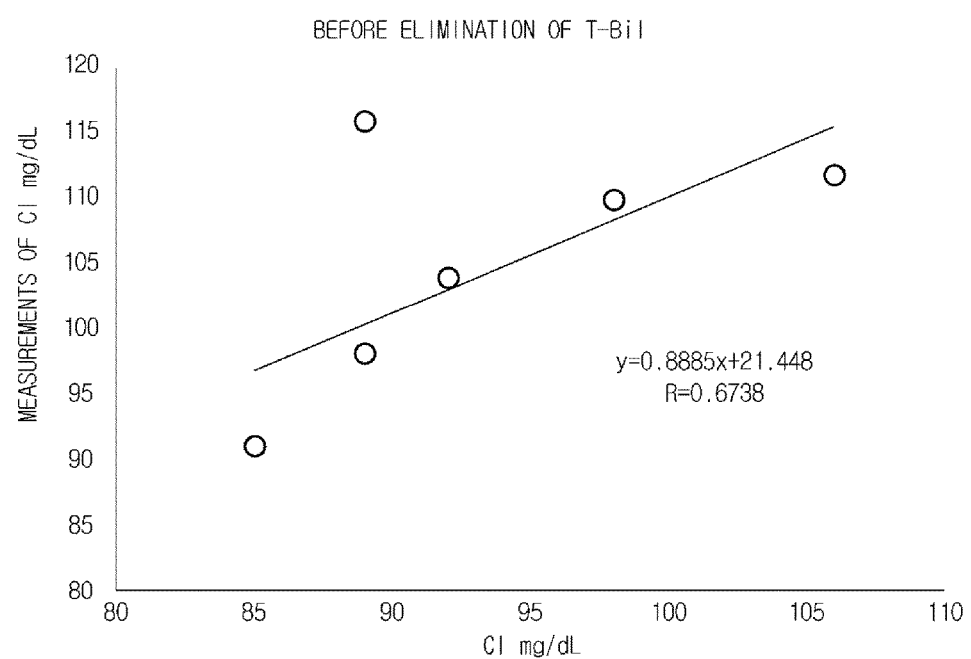
FIG. 26 shows a graph representing correlations of chloride concentrations before compensation for bilirubin interference.
Figure 27:
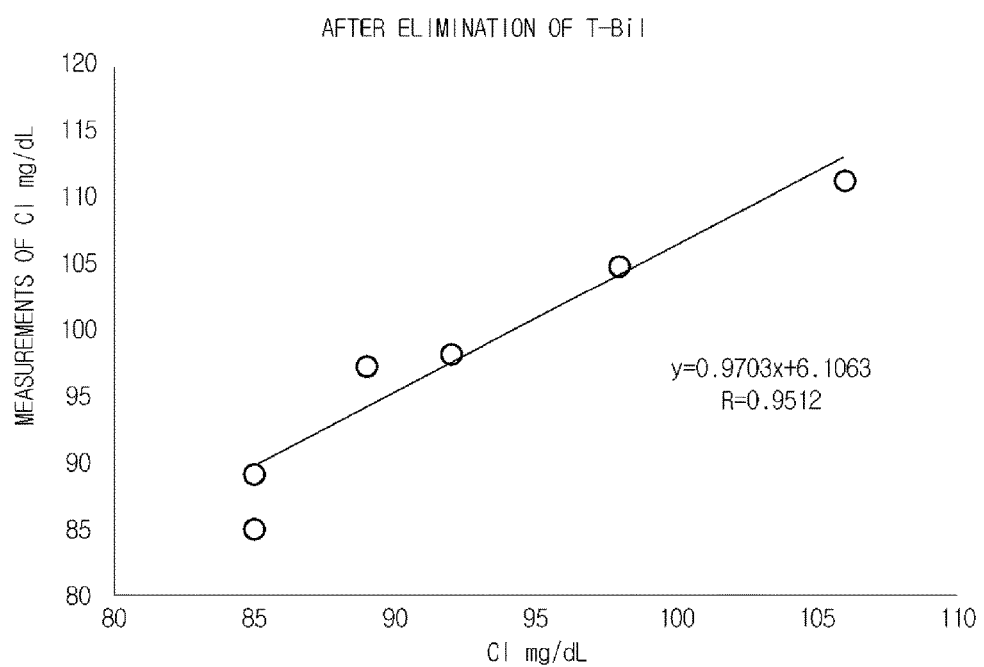
FIG. 27 shows a graph representing correlations of chloride concentrations after compensation for bilirubin interference.

FIG. 26 shows a graph representing correlations of chloride concentrations before compensation for bilirubin interference, and FIG. 27 shows a graph representing correlations of chloride concentrations after compensation for bilirubin interference.

The graphs shown in FIGS. 26 and 27 are produced based on experimental results represented in the table of FIG. 25. The Y-axis of the graph of FIG. 26 represents chloride concentrations measured by the test device 100 before compensation for the bilirubin interference, e.g., $C_{tgt}$, and the Y-axis of the graph of FIG. 27 represents chloride concentrations measured by the test device 100 after elimination of the bilirubin interference, e.g., $C_{Eff}$. The X-axis of both graphs represents chloride concentrations measured by the standard device.

It is seen that correlations appear not to be good with a correlation coefficient being no more than 0.6738 before compensation for the bilirubin interference, as shown in FIG. 26, but they appear to be better with an increased correlation coefficient being 0.9512 after compensation for the bilirubin interference, as shown in FIG. 27.

In the meantime, the chamber 200 in accordance with an exemplary embodiment has a structure in which the concentration of total bilirubin is more accurately measured or the bilirubin interference is more effectively eliminated. It will be described below in more detail.

In the following description, chambers 200a, 200c, 200d, 200e, 200f, 200g, 200h are only examples to implement the chamber 200 in accordance with an exemplary embodiment, e.g., the chamber 200 is considered to include all those chambers 200a, 200c, 200d, 200e, 200f, 200g, 200h.

Figure 28:
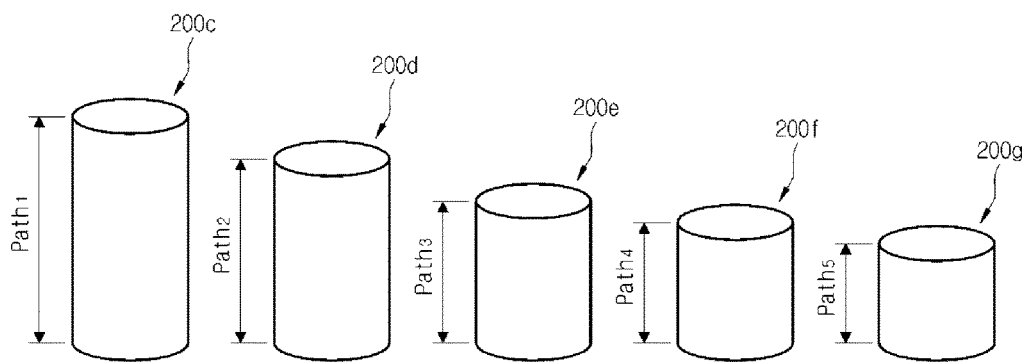
FIG. 28 shows a chamber structure, according to an exemplary embodiment.
Figure 29:
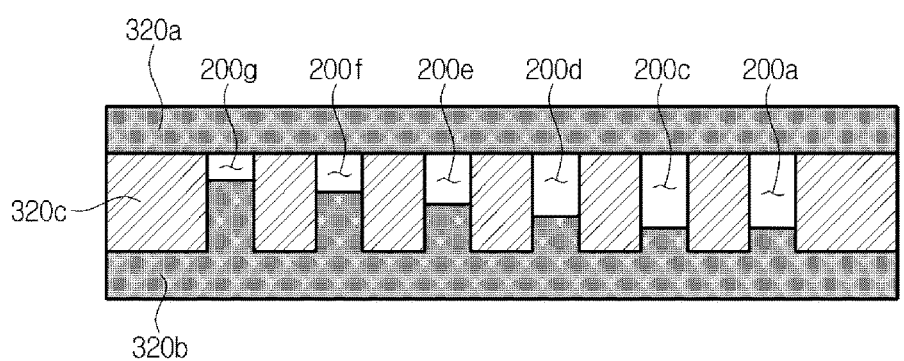
FIG. 29 is a view of appearance of a microfluidic device of a cartridge type having the chamber structure of FIG. 28.
Figure 30:
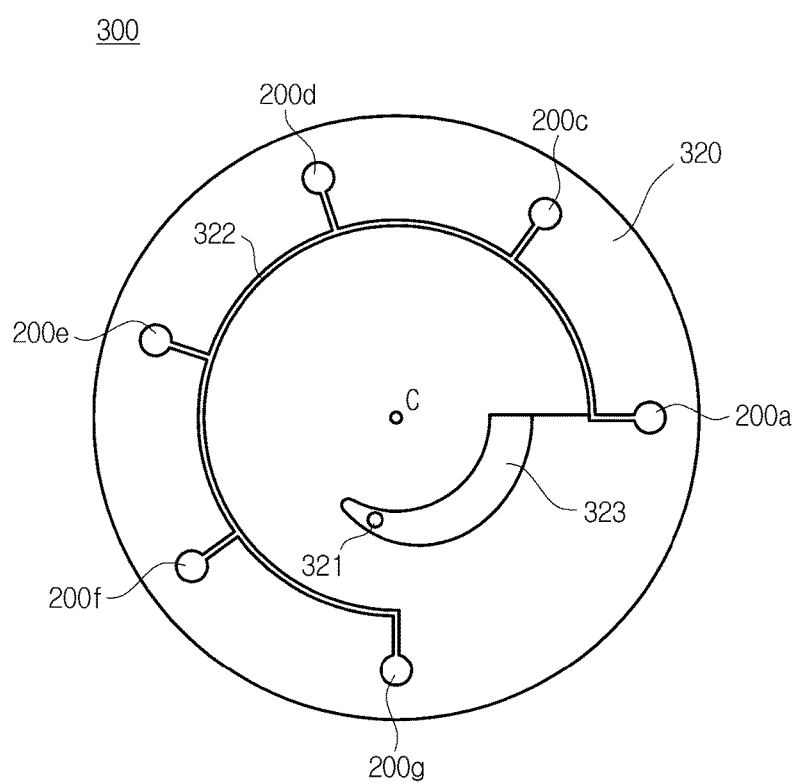
FIG. 30 is a cross-sectional view of the microfluidic device of FIG. 29 cut in AA' direction.

FIG. 28 shows a chamber structure, according to an exemplary embodiment, FIG. 29 is a view of appearance of a microfluidic device of a cartridge type having the chamber structure of FIG. 28, and FIG. 30 is a cross-sectional view of the microfluidic device of FIG. 29 cut in AA' direction.

In measuring optical characteristic values, a light path may influence the measurement results. For example, in measuring the concentration of bilirubin, a light path having the length of 3 mm or less may help to accurately measure higher concentrations, and a light path having the length of 3 mm or more may help to accurately measure lower concentrations.

Accordingly, in an exemplary embodiment, the chamber 200 may include a plurality of chambers 200c, 200d, 200e, 200f, 200g with respective light paths $Path_1$, $Path_2$, $Path_3$, $Path_4$, $Path_5$ of different lengths, as shown in FIG. 28, in order to apply a light path of a proper length for a concentration range of bilirubin present in the sample.

The chamber 200c having light path 1 ($Path_1$) is called chamber 1, the chamber 200d having light path 2 ($Path_2$) is called chamber 2, the chamber 200e having light path 3 ($Path_3$) is called chamber 3, the chamber 200f having light path 4 ($Path_4$) is called chamber 4, and the chamber 200f having light path 5 ($Path_5$) is called chamber 5.

Although the number of chambers in this exemplary embodiment is five, there may be more or less chambers than five as long as the chambers have different light paths in length.

As shown in FIGS. 29 and 30, the plurality of chambers 200c, 200d, 200e, 200f, 200g with different light paths in length $Path_1$, $Path_2$, $Path_3$, $Path_4$, $Path_5$ may be formed on the platform 320 of the microfluidic device 300, and in a case that a substance other than bilirubin is a target substance, the target substance detection chamber 200a may further be formed to measure the concentration of the target substance. The length of the light path of the target substance detection chamber 200a may or may not be the same as that of one of the plurality of chambers 200c, 200d, 200e, 200f, 200g.

The target substance detection chamber 200a may contain a reagent used to measure the concentration of the target substance. However, in the case the concentration of the target substance is measured only by optical measurement, the target substance detection chamber 200a may not contain the reagent. The plurality of chambers 200c, 200d, 200e, 200f, 200g do not contain a reagent for measuring the concentration of bilirubin.

For example, to form the plurality of chambers 200c, 200d, 200e, 200f, 200g having different light paths $Path_1$, $Path_2$, $Path_3$, $Path_4$, $Path_5$ in length, the bottom plate 320b of the respective chambers may be formed differently in terms of thickness, as shown in FIG. 30. For a chamber having a shorter light path, the thickness of the bottom plate 320b may be formed to be thicker, and for a chamber having a longer light path, the thickness of the bottom plate 320b may be formed to be thinner.

In this exemplary embodiment, the thickness of the bottom plate 320b for chamber 5 200g may be formed to be thickest, and the thickness of the bottom plate 320b for chamber 1 200a may be formed to be thinnest.

Figure 31:
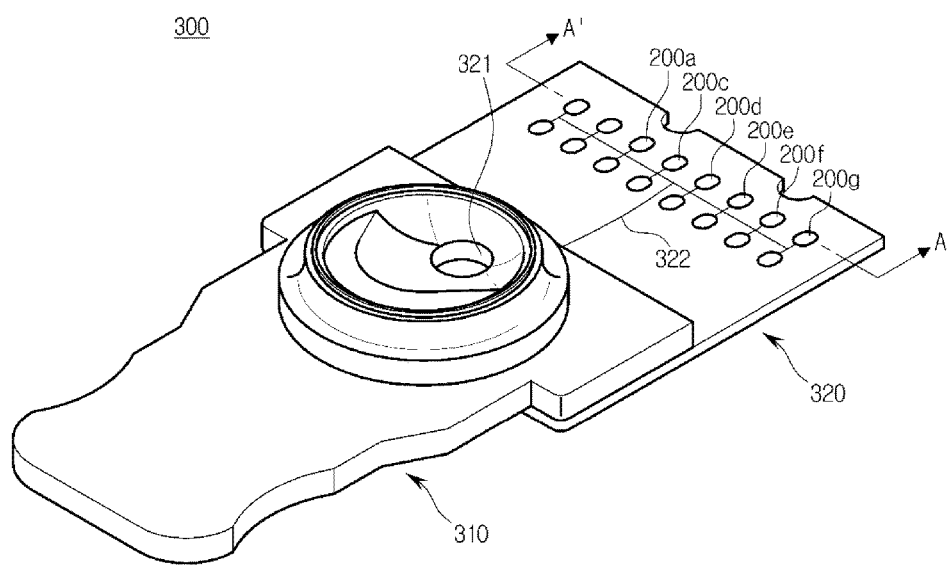
FIG. 31 is a view of appearance of another microfluidic device having the chamber structure of FIG. 28.

FIG. 31 is a view of appearance of another microfluidic device having the chamber structure of FIG. 28.

Even in the case that the microfluidic device 300 is implemented in a disc type, as shown in FIG. 31, the plurality of chambers 200c, 200d, 200e, 200f, 200g with different light paths in length $Path_1$, $Path_2$, $Path_3$, $Path_4$, $Path_5$ may be formed on the platform 320 of the microfluidic device 300, and in a case a substance other than bilirubin is a target substance, the target substance detection chamber 200a may further be formed to measure the concentration of the target substance.

Figure 32:
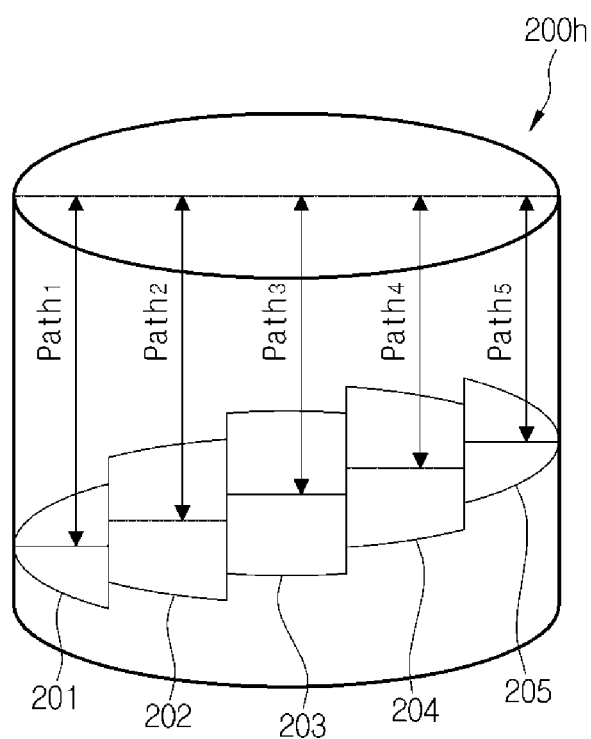
FIG. 32 shows a chamber structure, according to another exemplary embodiment.
Figure 33:
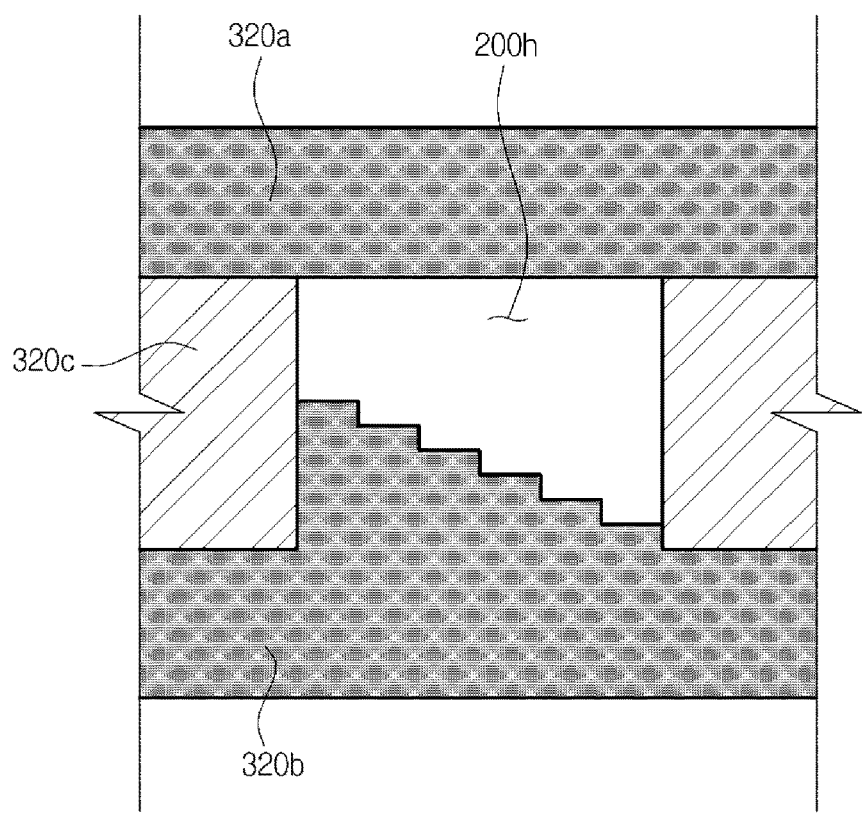
FIG. 33 is a cross-sectional view of a microfluidic device having the chamber structure of FIG. 32.

FIG. 32 shows a chamber structure, according to another exemplary embodiment, and FIG. 33 is a cross-sectional view of a microfluidic device having the chamber structure of FIG. 32.

As shown in FIG. 32, it is also possible for a single chamber 200h to have different light paths $Path_1$, $Path_2$, $Path_3$, $Path_4$, $Path_5$ in length using steps 201, 202, 203, 204, and 205 having different depths. In this case, since measurements for different light paths may be obtained with the single chamber 200h, the microfluidic device or the test device may be miniaturized with the chamber 200h.

In order to form the light paths $Path_1$, $Path_2$, $Path_3$, $Path_4$, $Path_5$ with different lengths within the single chamber 200h, steps may be formed on the floor of the chamber 200h. A lowest step 201 on the bottom of the chamber 200h forms the longest light path $Path_1$, and a highest step 205 forms the shortest light path $Path_5$.

The chamber 200h in the exemplary embodiment of FIG. 32 may be included in the microfluidic device 300 of both cartridge type and disc type.

For example, in the case the chamber 200h is included in the microfluidic device 300 of a cartridge type, steps corresponding to the plurality of light paths may be formed on the bottom plate 320b that forms the single chamber 200h, as shown in FIG. 33.

It is also possible for the aforementioned chamber 200 not to be included in the microfluidic device 300 but to be implemented in the cuvette type such that the chamber 200 may be mounted directly on the test device 100.

Operations of the test device 100 for accurately measuring the concentration of bilirubin present in the sample or efficiently eliminating the bilirubin interference based on the chambers 200c, 200d, 200e, 200f, 200g, 200h will now be described.

Once the plurality of chambers 200c, 200d, 200e, 200f, 200g, or the single chamber 200h having different light paths, or the microfluidic device 300 having them is mounted on the test device 100, the light source 111 irradiates light to the respective light paths. The irradiated light may have a wavelength in the 400 nm, 500 nm, or 600 nm band, or may have an arbitrary wavelength.

Specifically, once the plurality of chambers 200c, 200d, 200e, 200f, 200g, or the microfluidic device 300 having them is mounted on the test device 100, the same wavelength of light is irradiated to the respective chambers 1, 2, 3, 4, and 5 200c, 200d, 200e, 200f, and 200g, and the detector 112 detects the respective light transmitted through them and converts them to respective optical characteristic values. It is assumed herein that the transmitted light is converted to optical density.

Alternatively, once a single chamber 200h having many different light paths or the microfluidic device 300 having the chamber 200h is mounted on the test device 100, the same wavelength of light is irradiated for the light paths 1 to 5 Path1 to Path5 formed on the chamber 200h, and the detector 112 detects light transmitted through the respective light paths and converts them to respective optical densities.

The data processor 130 may measure linearity using the measured optical densities for the respective light paths, and select a light path to be used in measuring an optical density of bilirubin or an optical density of a measurement item based on the measurement result of linearity.

Figure 34A:
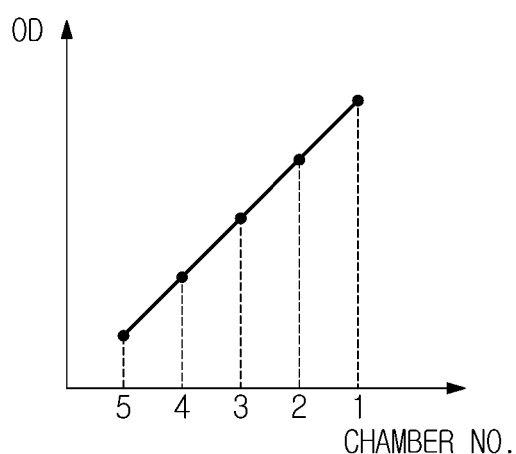
FIGS. 34A and 34B show a schematic graph representing measurable results of linearity of light paths shown in FIG. 28.
Figure 34B:
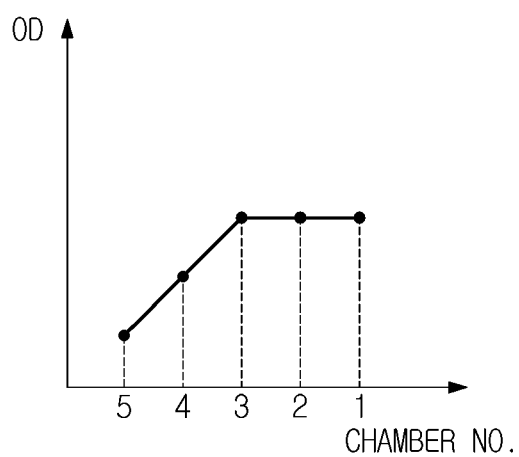

FIGS. 34A and 34B show a schematic graph representing measurable results of linearity of light paths shown in FIG. 28.

In general, the longer the light path, the higher the confidence in the measured optical characteristic value, so the data processor 130 may select a longest light path within a range that meets linearity as a light path to be used for measurement of the optical density of bilirubin.

For example, if all the optical densities for the light paths 1 to 5 satisfy linearity, as shown in FIG. 34A, the data processor 130 may select the longest light path 1.

Alternatively, if only the optical densities for the light paths 3, 4, and 5 satisfy linearity while the optical densities for the light paths 1 and 2 do not, as shown in FIG. 34B, the data processor 130 may select the longest light path 3 among the light paths that satisfy linearity.

Furthermore, the data processor 130 may determine the concentration of total bilirubin present in the sample using the optical densities measured in the 400 nm, 500 nm, and 600 nm bands, equation 2, and the calibration curve, for the selected light path.

Or, the data processor 130 may determine the concentration of the target substance resulting from compensation for the bilirubin interference, using optical densities measured in the 400 nm, 500 nm, and 600 nm bands, equation 2, the calibration curve for a measurement item, and equation 4, for the selected light path.

Or, the data processor 130 may determine the concentration of a measurement item resulting from compensation for the bilirubin interference, using optical densities measured in the 400 nm, 500 nm, and 600 nm bands, equation 2, equation 5, and the calibration curve for the measurement item, for the selected light path.

The aforementioned exemplary embodiments of the light path and chamber structure may, of course, be applied even in the case that the target substance or the interfering substance is not bilirubin.

For example, even in a case that the target substance is GGT, one of the plurality of light paths may be selected, and the GGT level may be determined using an optical density measured in the selected optical density.

According to the exemplary embodiments of the sample test method, test device, and chambers, interference of an interfering substance present in the sample may be compensated for based on optical measurement without addition of any reagent for measuring the interfering substance.

Furthermore, even in a section where the target substance has a low concentration, the interference of an interfering substance may be effectively compensated for, and even if the sample is used for tests without dilution, trustworthy test results may be obtained.

Moreover, the concentration of total bilirubin may be quantitatively measured, and the bilirubin interference may be effectively and accurately compensated for from a result of measuring other measurement item than bilirubin.

Several exemplary embodiments have been described, but a person of ordinary skill in the art will understand and appreciate that various modifications can be made without departing the scope of exemplary embodiments of the inventive concept. Thus, it will be apparent to those ordinary skilled in the art that the true scope of technical protection is only defined by the following claims and their equivalents.

What is claimed is:

1. A sample test method comprising:
    measuring an optical characteristic value of a target substance present in a sample;
    measuring an optical characteristic value of an interfering substance present in the sample; and
    determining a concentration of the target substance for which interference of the interfering substance is compensated for based on the optical characteristic value of the interfering substance,
    wherein the determining the concentration of the target substance for which interference of the interfering substance is compensated for comprises:
    determining the concentration of the target substance based on the optical characteristic value of the target substance, and
    determining the concentration of the interfering substance based on the optical characteristic value of the interfering substance, and
    compensating the concentration of the target substance using the concentration of the interfering substance.

2. The sample test method of claim 1, wherein the compensating the concentration of the target substance comprises:
    applying a fluctuation coefficient to the concentration of the interfering substance to obtain an application result, and then subtracting or adding the application result from or to the concentration of the target substance.

3. The sample test method of claim 1,
    wherein the measuring the optical characteristic value of the target substance comprises:
    measuring optical characteristic values of the target substance at a main wavelength and a sub-wavelength; and
    subtracting the optical characteristic value at the sub-wavelength from the optical characteristic value at the main wavelength.

4. The sample test method of claim 1, wherein the sample includes blood, and
    wherein the target substance includes gamma-glutamyl transferase (GGT).

5. The sample test method of claim 1, wherein the interfering substance includes bilirubin.

6. The sample test method of claim 1, wherein the measuring the optical characteristic value of the interfering substance is done without presence of a reagent for reacting with the interfering substance.

7. The sample test method according to claim 1, wherein the optical characteristic value of the target substance is representative of concentration amount of the target substance and the optical characteristic value of the interfering substance is representative of concentration amount of the interfering substance, and
    the sample test method is performed using one or more processors.

8. A test device comprising:
    a measurer configured to measure an optical characteristic value of a target substance present in a sample and an optical characteristic value of an interfering substance present in the sample; and
    a data processor configured to determine a concentration of the target substance for which interference of the interfering substance is compensated for based on the optical characteristic value of the interfering substance,
    wherein the data processor is configured to determine the concentration of the target substance based on the optical characteristic value of the target substance, and determine the concentration of the interfering substance based on the optical characteristic value of the interfering substance, and compensate the concentration of the target substance using the concentration of the interfering substance.

9. The test device of claim 8, wherein the data processor is configured to apply a fluctuation coefficient to the concentration of the interfering substance to obtain an application result, and then subtract or add the application result from or to the concentration of the target substance.

10. The test device of claim 8,
    wherein the measurer is configured to the measure optical characteristic value of the target substance at a main wavelength and a sub-wavelength, and
    wherein the data processor is configured to subtract the optical characteristic value measured at the sub-wavelength from the optical characteristic value measured at the main wavelength.

11. The test device of claim 8, wherein the sample includes blood, and
    wherein the target substance includes gamma-glutamyl transferase (GGT).

12. The test device of claim 11, wherein the interfering substance includes bilirubin.

13. The test device of claim 8,
    wherein the measurer is configured to measure optical characteristic value of the sample at a plurality of wavelengths, and
    wherein the data processor is configured to determine a final optical characteristic value as a difference between two or more of the measured optical characteristic values which were measured at a plurality of wavelengths,
    wherein the final optical characteristic value is an optical characteristic value for the interfering substance.

* * * * *